(12) United States Patent
Calderon Oliveras et al.

(10) Patent No.: US 11,000,653 B2
(45) Date of Patent: May 11, 2021

(54) INHALER

(71) Applicant: Norton (Waterford) Limited, Waterford (IE)

(72) Inventors: Enrique Calderon Oliveras, Waterford (IE); Daniel Buck, Waterford (IE); Erica Jamie Kantor, Cambridge (GB); Ross William Weir, Cambridge (GB); James Roche, Enniscorthy (IE); Steven David Gardner, Peterborough (GB); Robert Owen Kivlin, Cambridge (GB)

(73) Assignee: Norton (Waterford) Limited, Waterford (IE)

( * ) Notice: Subject to any disclaimer, the term of this patent is extended or adjusted under 35 U.S.C. 154(b) by 460 days.

(21) Appl. No.: 15/704,444

(22) Filed: Sep. 14, 2017

(65) Prior Publication Data
US 2018/0140788 A1  May 24, 2018

Related U.S. Application Data

(60) Provisional application No. 62/424,299, filed on Nov. 18, 2016.

(51) Int. Cl.
*A61M 15/00* (2006.01)
*A61B 5/00* (2006.01)

(52) U.S. Cl.
CPC ....... *A61M 15/0023* (2014.02); *A61B 5/4833* (2013.01); *A61M 15/0025* (2014.02);
(Continued)

(58) Field of Classification Search
CPC ............ A61M 16/008; A61M 16/0001; A61M 16/0023; A61M 16/0025;
(Continued)

(56) References Cited

U.S. PATENT DOCUMENTS 5,069,204 A * 12/1991 Smith ............... A61M 15/0068
128/200.23
5,482,030 A * 1/1996 Klein .................. A61M 15/009
116/308

(Continued)

FOREIGN PATENT DOCUMENTS

EP    1135056 B1    8/2006
EP    1992381 A1    11/2008
(Continued)

*Primary Examiner* — Joseph D. Boecker
*Assistant Examiner* — Thomas W Greig
(74) *Attorney, Agent, or Firm* — Flaster Greenberg, P.C.

(57) ABSTRACT

The introduction of electronics into a drug delivery device may introduce certain technical challenges, such as durability, electro-mechanical integration, and drug delivery performance. The present disclosure provides solutions for inclusion of an electronics module with an inhaler. For example, heat stakes may be used to secure a printed circuit board (PCB) to an electronics module's housing. Also for example, a slider may be used to transfer vertical movement of an inhaler's yoke to an electronics module's switch. Also for example, certain seals may be used when interfacing the electronics module to other portions of the device's housing to achieve a desired performance.

26 Claims, 13 Drawing Sheets

(52) U.S. Cl.
CPC .... *A61M 15/0065* (2013.01); *A61M 15/0086* (2013.01); *A61M 15/009* (2013.01); *A61M 15/0021* (2014.02); *A61M 15/0096* (2014.02); *A61M 2202/064* (2013.01); *A61M 2205/3569* (2013.01); *A61M 2205/50* (2013.01); *A61M 2205/502* (2013.01); *A61M 2205/8206* (2013.01); *A61M 2205/8212* (2013.01)

(58) Field of Classification Search
CPC ....... A61M 15/00–085; A61M 15/0021–0026; A61M 15/0068–0083; A61M 15/009; A61M 15/008; A61M 15/0001
See application file for complete search history.

(56) References Cited

U.S. PATENT DOCUMENTS

| | | |
|---|---|---|
| 5,839,429 A | 11/1998 | Marnfeldt et al. |
| 5,842,468 A | 12/1998 | Denyet et al. |
| 5,887,586 A | 3/1999 | Dahlback et al. |
| 6,082,358 A * | 7/2000 | Scarrott ............ A61M 15/0065 128/200.14 |
| 6,142,339 A * | 11/2000 | Blacker ............... A61M 15/009 222/23 |
| 6,202,642 B1 | 3/2001 | McKinnon et al. |
| 6,285,731 B1 | 9/2001 | Marnfeldt et al. |
| 6,390,088 B1 | 5/2002 | Sprenger et al. |
| 6,958,691 B1 | 10/2005 | Anderson et al. |
| 6,978,780 B1 | 12/2005 | Marnfeldt et al. |
| 6,990,975 B1 | 1/2006 | Jones et al. |
| 7,072,738 B2 | 7/2006 | Bonney et al. |
| 7,151,456 B2 | 12/2006 | Godfrey et al. |
| 7,191,777 B2 | 3/2007 | Brand et al. |
| 7,198,172 B2 | 4/2007 | Harvey et al. |
| 7,233,228 B2 | 6/2007 | Lintell et al. |
| 7,249,687 B2 | 7/2007 | Anderson et al. |
| 7,347,200 B2 | 3/2008 | Jones et al. |
| 7,383,837 B2 | 6/2008 | Robertson et al. |
| 7,418,961 B2 * | 9/2008 | Jones ............... A61M 15/009 128/200.14 |
| 7,424,888 B2 | 9/2008 | Harvey et al. |
| 7,495,546 B2 | 2/2009 | Lintell et al. |
| 7,837,648 B2 | 11/2010 | Blair et al. |
| 8,231,573 B2 | 7/2012 | Edwards et al. |
| 8,240,301 B2 | 8/2012 | Spaargaren et al. |
| 8,424,517 B2 | 4/2013 | Sutherland et al. |
| 8,464,707 B2 | 6/2013 | Jongejan et al. |
| 8,547,239 B2 | 10/2013 | Peatfield et al. |
| 8,807,131 B1 | 8/2014 | Tunnell et al. |
| 8,960,189 B2 | 2/2015 | Morrison et al. |
| 8,997,735 B2 | 4/2015 | Zierenberg et al. |
| 9,056,174 B2 | 6/2015 | Bradshaw et al. |
| 9,174,009 B2 | 11/2015 | Peatfield et al. |
| 9,188,579 B2 | 11/2015 | Shen et al. |
| 9,242,056 B2 | 1/2016 | Andersen et al. |
| 9,339,616 B2 | 5/2016 | Denny et al. |
| 9,364,619 B2 | 6/2016 | Overfield et al. |
| 9,427,534 B2 | 8/2016 | Bruin et al. |
| 9,463,291 B2 | 10/2016 | Imran et al. |
| 9,468,729 B2 | 10/2016 | Sutherland et al. |
| 9,550,031 B2 | 1/2017 | Van Sickle et al. |
| 9,694,147 B2 | 7/2017 | Peatfield et al. |
| 9,736,642 B2 | 8/2017 | Ostrander et al. |
| 9,839,398 B2 | 12/2017 | Yamamori et al. |
| 9,911,308 B2 | 3/2018 | Edwards et al. |
| 9,956,360 B2 | 5/2018 | Germinario et al. |
| 9,962,507 B2 | 5/2018 | Germinario et al. |
| 9,962,508 B2 | 5/2018 | Bruin et al. |
| 10,016,134 B2 | 7/2018 | Hansen et al. |
| 10,046,121 B2 | 8/2018 | Kolb et al. |
| 2002/0047021 A1 * | 4/2002 | Blacker ................ G06M 1/041 222/23 |
| 2002/0128591 A1 | 9/2002 | Kleiner et al. |
| 2002/0185128 A1 | 12/2002 | Theobald et al. |
| 2003/0192535 A1 | 10/2003 | Christrup et al. |
| 2004/0089299 A1 | 5/2004 | Bonney et al. |
| 2004/0117062 A1 | 6/2004 | Bonney et al. |
| 2005/0119604 A1 | 6/2005 | Bonney et al. |
| 2005/0161467 A1 | 7/2005 | Jones et al. |
| 2005/0247312 A1 | 11/2005 | Davies et al. |
| 2005/0251289 A1 | 11/2005 | Bonney et al. |
| 2005/0268905 A1 * | 12/2005 | Rasmussen ......... A61M 15/009 128/200.23 |
| 2006/0254581 A1 * | 11/2006 | Genova ............. A61M 15/0065 128/200.23 |
| 2008/0017189 A1 | 1/2008 | Ruckdeschel et al. |
| 2008/0173301 A1 * | 7/2008 | Deaton ............. A61M 15/0091 128/203.12 |
| 2008/0178872 A1 * | 7/2008 | Genova ............. A61M 15/0065 128/200.23 |
| 2008/0230057 A1 | 9/2008 | Sutherland et al. |
| 2009/0139517 A1 * | 6/2009 | Wachtel ................ A61M 11/001 128/200.23 |
| 2009/0221308 A1 | 9/2009 | Lerner et al. |
| 2009/0308385 A1 * | 12/2009 | Brewer ............. A61M 15/0065 128/203.12 |
| 2010/0242960 A1 | 9/2010 | Zangerle et al. |
| 2010/0250280 A1 | 9/2010 | Sutherland et al. |
| 2011/0265788 A1 * | 11/2011 | Wu ...................... A61M 15/009 128/200.23 |
| 2011/0282693 A1 | 11/2011 | Craft et al. |
| 2013/0269685 A1 | 10/2013 | Wachtel et al. |
| 2014/0106324 A1 | 4/2014 | Adams et al. |
| 2014/0182584 A1 | 7/2014 | Sutherland et al. |
| 2015/0101599 A1 * | 4/2015 | Berry ................ A61M 15/0075 128/202.22 |
| 2015/0283341 A1 | 10/2015 | Adams et al. |
| 2016/0082208 A1 | 3/2016 | Ballam et al. |
| 2016/0128389 A1 | 5/2016 | Lamb et al. |
| 2016/0166766 A1 | 6/2016 | Schuster et al. |
| 2016/0228657 A1 | 8/2016 | Sutherland et al. |
| 2016/0256639 A1 | 9/2016 | Van Sickle et al. |
| 2016/0303336 A1 * | 10/2016 | Arp ...................... A61K 9/0075 |
| 2016/0314256 A1 | 10/2016 | Su et al. |
| 2016/0325057 A1 * | 11/2016 | Morrison ............ A61M 15/009 |
| 2017/0079557 A1 | 3/2017 | Lauk et al. |
| 2017/0109493 A1 | 4/2017 | Hogg et al. |
| 2017/0140125 A1 | 5/2017 | Hogg et al. |
| 2017/0164892 A1 | 6/2017 | Sezan et al. |
| 2017/0173279 A1 | 6/2017 | Sutherland et al. |
| 2017/0246406 A1 | 8/2017 | Sutherland et al. |
| 2017/0258993 A1 | 9/2017 | Pizzochero et al. |
| 2017/0262613 A1 | 9/2017 | Ljungberg et al. |
| 2017/0325734 A1 | 11/2017 | Sutherland et al. |
| 2017/0363673 A1 | 12/2017 | Mukherjee et al. |
| 2018/0011988 A1 | 1/2018 | Ziegler et al. |
| 2018/0052964 A1 | 2/2018 | Adelson et al. |
| 2018/0085540 A1 | 3/2018 | Dantsker et al. |
| 2018/0125365 A1 | 5/2018 | Hunter et al. |
| 2018/0161530 A1 | 6/2018 | Ganton et al. |
| 2019/0001085 A1 * | 1/2019 | Cottenden ........... A61M 15/009 |

FOREIGN PATENT DOCUMENTS

| | | | |
|---|---|---|---|
| EP | 3228345 A1 | 10/2017 | |
| GB | 2552720 A * | 2/2018 | .......... A61M 15/002 |
| WO | WO/1995/022365 A1 | 8/1995 | |
| WO | WO/1999/063901 A1 | 12/1999 | |
| WO | WO/2003/063754 A1 | 8/2003 | |
| WO | WO/2009/003989 A1 | 1/2009 | |
| WO | WO/2016/043601 A1 | 3/2016 | |
| WO | WO/2017/005605 A1 | 1/2017 | |
| WO | WO/2017/129521 A1 | 8/2017 | |
| WO | WO/2017/141194 A1 | 8/2017 | |
| WO | WO/2017/176693 A1 | 10/2017 | |
| WO | WO/2017/176704 A1 | 10/2017 | |
| WO | WO/2017/180980 A1 | 10/2017 | |
| WO | WO/2017/189712 A1 | 11/2017 | |
| WO | WO/2017/051389 A1 | 7/2018 | |
| WO | WO/2018/128976 A1 | 7/2018 | |

(56) References Cited

FOREIGN PATENT DOCUMENTS

WO     WO2018/134552 A1    7/2018
WO     WO/2018/134553 A1   7/2018

\* cited by examiner

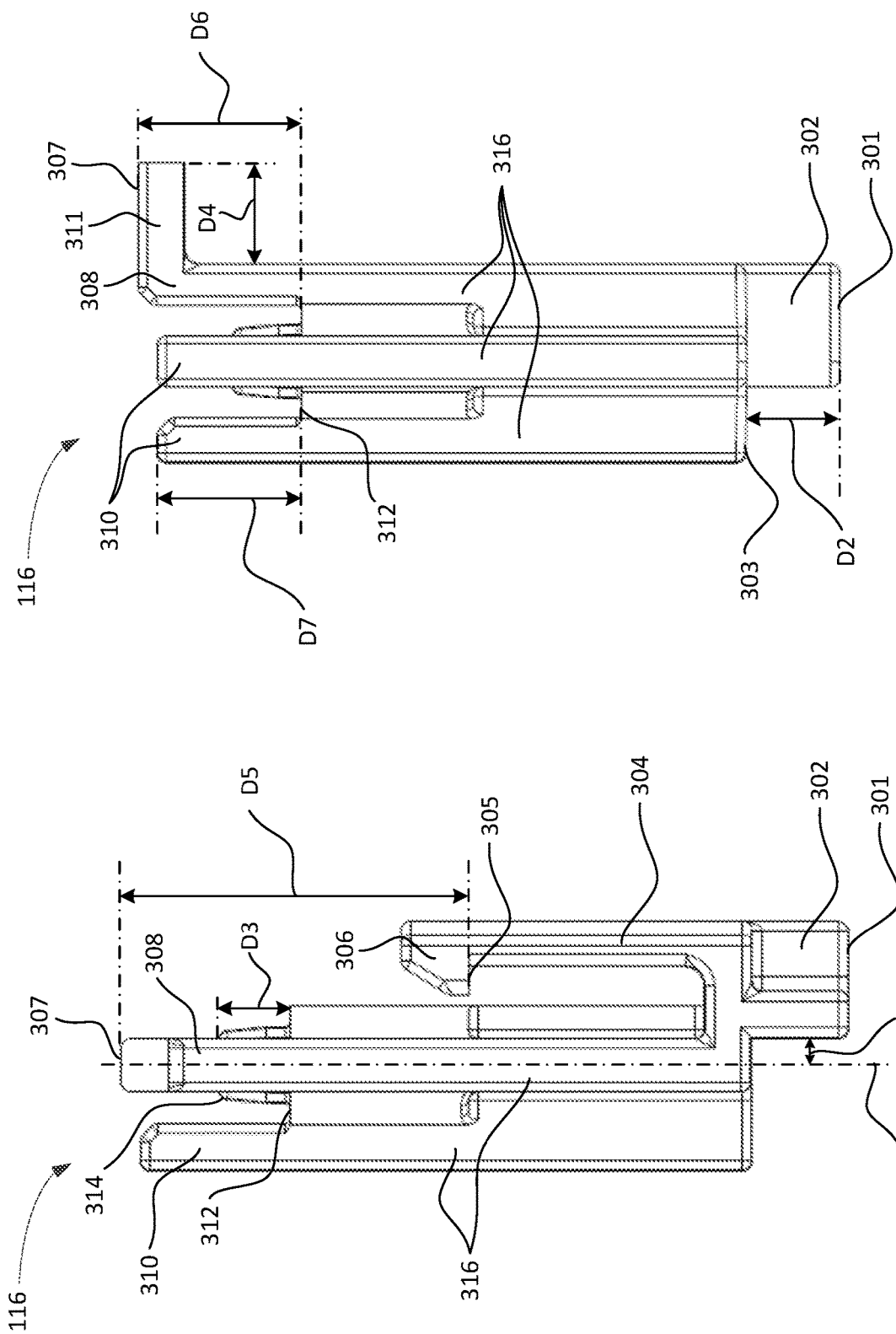

INHALER

CROSS-REFERENCE TO RELATED APPLICATIONS

This application claims the benefit of U.S. Provisional Patent Application No. 62/424,299, filed Nov. 18, 2016, the contents of which are incorporated by reference herein.

BACKGROUND

Drug delivery devices facilitate the delivery of medication into a patient's body via various routes of administration. Typical routes of administration include oral, topical, sublingual inhalation, injection and the like. The devices may be used to deliver medications for the treatment various diseases, ailments and medical conditions. Inhalation devices, for example, may be used to treat asthma, chronic obstructive pulmonary disease (COPD) and cystic fibrosis (CF). While drug delivery devices are designed to deliver an appropriate dose of medication to a patient as part of a therapeutic treatment, the effectiveness of a particular treatment may be influenced by non-physiological factors, such as the patient's adherence and compliance.

In the context of a drug therapy, adherence may refer to the degree to which a patient is following a prescribed dosing regimen. For example, if the patient's prescription calls for two doses each day, and the patient is taking two doses per day, the patient may be considered 100% adherent. If the patient is only taking one dose per day, he or she may be deemed only 50% adherent. In the latter case, the patient may not be receiving the treatment prescribed by his or her doctor, which may negatively affect the efficacy of the therapeutic treatment.

Compliance may refer to a patient's technique when using a particular drug delivery device. If the patient is using the device in a manner that is recommended by a doctor or by a manufacturer, the device is likely to deliver the desired dose of medication and the patient may be deemed compliant. However, if the device is not being used properly during drug administration, the device's ability to deliver a proper dose of medication may be compromised. As such, the patient may be deemed non-compliant. In the case of an inhalation device, for example, the patient may need to achieve a minimum inspiratory effort to ensure a full dose of medication is delivered from the device into the patient's lungs. For some patients, such as children and the elderly, meeting the requirements for full compliance may be difficult due to physical limitations, such as limited lung function. Accordingly, like adherence, failing to achieve full compliance may reduce the effectiveness of a prescribed treatment.

A patient's ability to achieve full compliance may be further complicated by certain physical properties of the medication. For example, some respiratory medications may consist of fine particles and/or may lack any odor or taste. Thus, a patient using an inhalation device may not be able to correct a non-compliant use because he or she may not be able to immediately detect or sense that medication is being inhaled and/or know whether the amount of inhaled medication complies with the prescription.

SUMMARY

To improve adherence and compliance, a drug delivery device may be adapted to include an electronics module that is configured to sense, track and/or process usage conditions and parameters associated with the device. The electronics module may be further configured to communicate the conditions and parameters to external devices, such as a smartphone, for similar and/or further processing. The inclusion of an electronics module in a drug delivery device opens the door to a wealth of digital improvements and features to enhance the use of the device. The electronics module, in this context, may create a platform to leverage helpful smartphone applications and powerful data analytics. However, the introduction of electronics into any drug delivery device may introduce certain technical challenges, such as durability, electro-mechanical integration, and drug delivery performance. The present disclosure provides solutions for inclusion of certain electrical components with a drug delivery device, such as an inhaler.

Examples of inhalation devices (e.g., breath-actuated inhalers) are provided herein. An exemplary inhaler may include heat stakes for securing a printed circuit board (PCB) to an electronics module's housing, such as a module cap. The heat stakes may be configured to partially deform when securing the PCB to the housing. The use of heat stakes may improve the inhaler's durability, including for example, reducing the risk of the electronics module becoming damaged or inoperable as a result of the inhaler being dropped. The use of heat stakes to fasten the PCB to the cap may reduce manufacturing costs and/or manufacturing time.

Also for example, a slider may be used to transfer vertical movement of an inhaler's yoke to an electronics module's switch. The movement of the inhaler's yoke may be associated with typical inhaler operation, for example the yoke may move in connection with the opening and closing of the inhaler's mouthpiece cover. Here, the slider may effectively integrate the electronics module into an operation that is familiar to the user, improving the overall electro-mechanical integration of the inhaler. That is, activation of the electronics module may be transparent to the user as the user operates the inhaler.

Also for example, certain seals may be used or formed when interfacing the electronics module to other portions of the inhaler's housing to achieve a desired performance. The electronics module may include a pressure sensor to measure pressure changes within the inhaler. These pressure changes may be used to calculate or determine aspects of the inhaler's operational performance, such as an air flow rate through the air flow path of the inhaler. Sealing, as described herein, may ensure effective translation of measured pressure changes to the operational performance parameters of the inhaler.

BRIEF DESCRIPTION OF THE DRAWINGS

FIGS. 4A-B show projection views of an example slider of an electronics module for an inhaler.

The present disclosure describes devices, systems, and methods for incorporating electronics with a drug delivery device and for sensing, tracking and/or processing usage conditions and parameters associated with the device. The devices, systems and methods are described in the context of a breath-actuated, dry powder inhaler (DPI). However, the described solutions are equally applicable to other drug delivery devices, such as an injector, a metered-dose inhaler, a nebulizer, a transdermal patch, or an implantable.

Figure 1A:
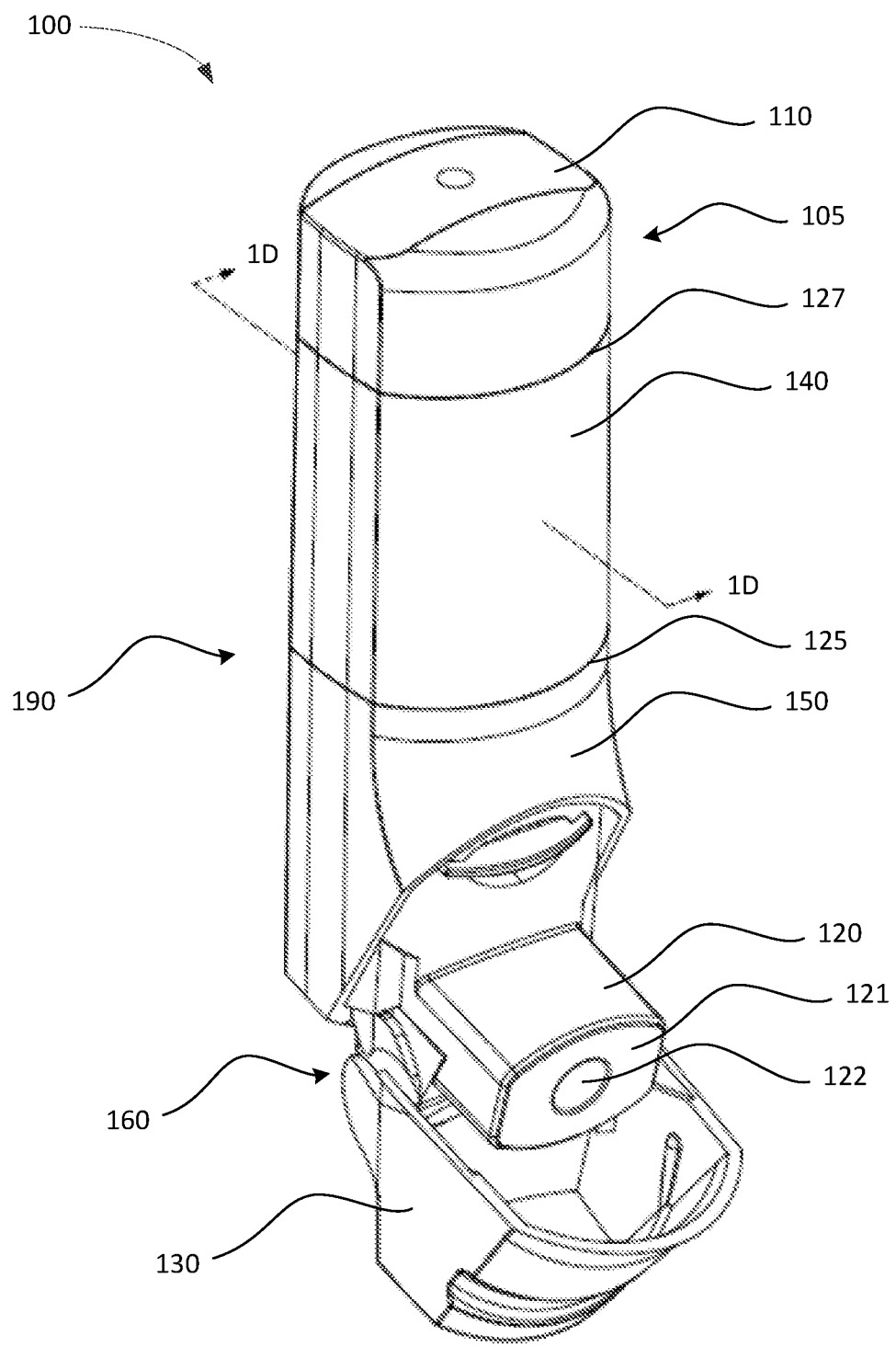
FIG. 1A is a perspective view of an example inhaler with an electronics module.

FIGS. 1A-1D show various views of an example inhaler 100 with an electronics module 105. FIG. 1A is a perspective view of the example inhaler 100. The inhaler 100 may be any type of respiratory device for delivering a specific amount of aerosolized medicament to a patient's lungs. As will be further discussed below, the inhaler 100 may include the electronics module 105 to monitor when and how patients are using the inhaler 100.

The inhaler 100 may include a housing 190. The housing 190 may house the mechanical and/or electrical components for facilitating the effective delivery of a medicament. The housing 190 may include a lower housing 150 and an upper housing 140.

The lower housing 150 may include a mouthpiece 120 extending therefrom. A mouthpiece cover 130 may be included for covering the mouthpiece 120 when the inhaler 100 is not in use. The mouthpiece cover 130 may be attached to the inhaler 100 via a hinge mechanism 160, which may enable the mouthpiece cover 130 to swing between open and closed positions. The hinge mechanism 160 may transfer motion of the mouthpiece cover 130 to one or more other parts within the housing 190 of the inhaler 100. As discussed below, this transfer of motion may be used to effect operation of other aspects of the inhaler 100, including for example, operation of the electronics module 105.

The mouthpiece 120 may have a surface 121. The surface 121 may define an opening 122. The opening 122 may be an opening to a conduit or air flow path 189 (e.g., as shown in FIG. 1D). The surface 121 may also define one or more bypass ports (e.g., the bypass ports shown in FIG. 6 and described later herein). Bypass ports may enable air to flow independent of the air flow path such that when a patient breathes-in or inhales, a portion of the air inhaled by the patient is not from the air flow path 189. In the case of a breath-actuated inhaler, for example, the bypass ports may be used to reduce the flow rate dependence of the inhaler 100 and/or to deliver an appropriate dose of medicament at lower flow rates through the air flow path 189.

DETAILED DESCRIPTION

The upper housing 140 may interface with the lower housing 150. The upper housing 140 and the lower housing 150 may be removably or permanently attached to one another, thereby forming a seal 125. The housing 190 may also include the electronics module 105. The electronics module 105 may have a cap 110 (e.g., an electronics module cap) that interfaces with the upper housing 140. The cap 110 and the upper housing 140 may be removably or permanently attached to one another, thereby forming a seal 127.

Figure 1B:
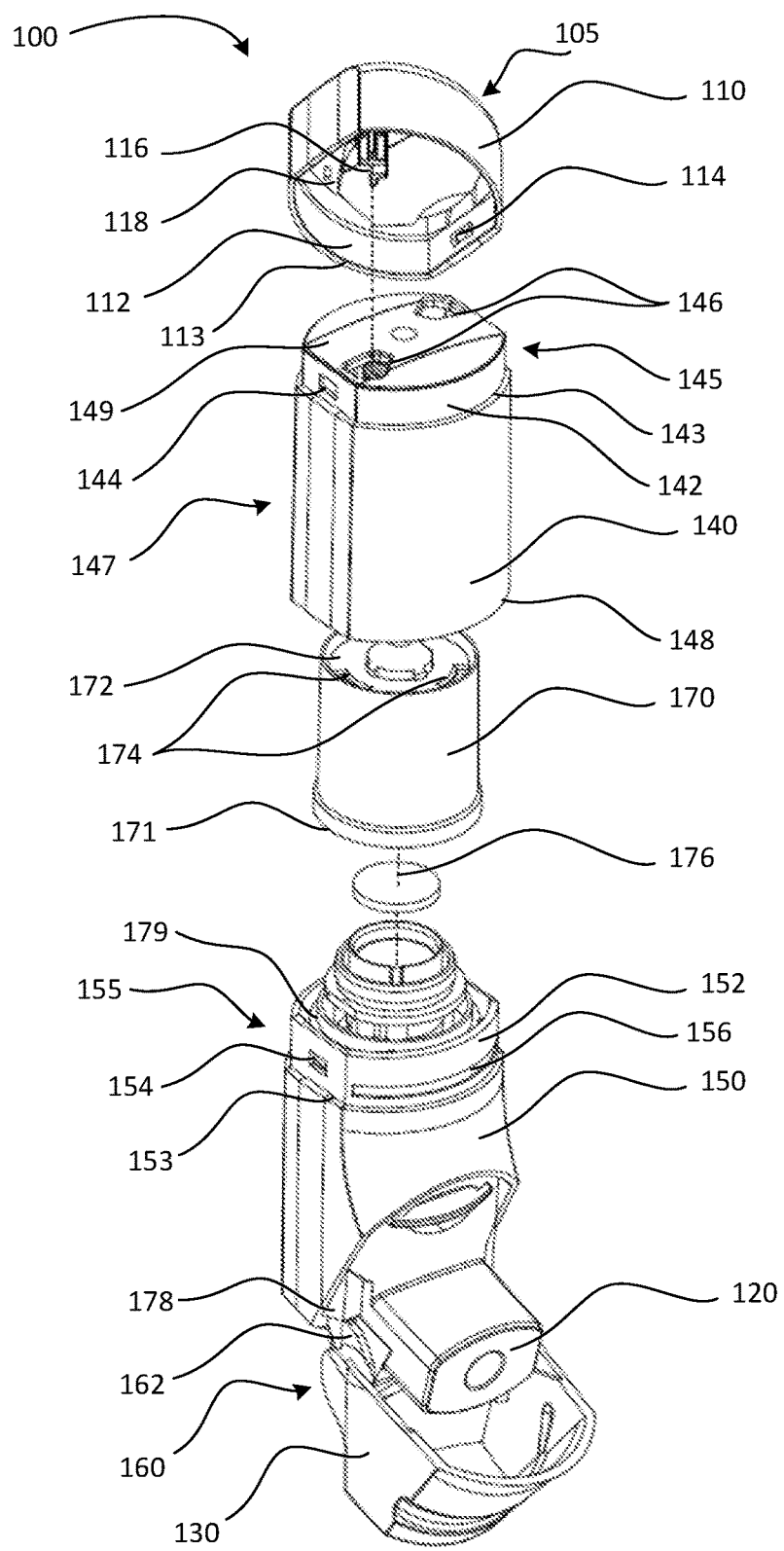
FIG. 1B shows a partially-exploded view of an example inhaler with an electronics module.

FIG. 1B shows a partially exploded view of the inhaler 100, including the interface between the upper housing 140 and the lower housing 150. In particular, the lower housing 150 may have a top portion 155 that defines an upper exterior surface 152. The upper exterior surface 152 may include a seal 156, which may be a labyrinth seal. The upper exterior surface 152 may be received in the upper housing 140 and overlap with at least a portion of a lower interior surface of the upper housing 140. The lower housing 150 may define a rim 153, which may abut a bottom edge 148 of the upper housing 140 when the lower housing 150 and the upper housing 140 are connected to one another. The interface between the bottom edge 148 and the rim 153 may define the seal 125 (e.g., as shown in FIG. 1A).

The lower housing 150 may also define one or more recesses 154, which may be configured to receive respective one or more clips or protrusions (not shown) on the lower interior surface of the upper housing 140. The coupling of the one or more recesses 154 with the one or more clips or protrusions may further prevent or inhibit the upper housing 140 from detaching from the lower housing 150.

FIG. 1B further depicts the interface between the upper housing 140 and the cap 110. More specifically, the cap 110 may define an inner peripheral surface 112 and an edge 113, which may be chamfered. The cap 110 may further include one or more clips or protrusions 114 extending from the inner peripheral surface 112. The upper housing 140 may define a top portion 145 having a first cross sectional area and a bottom portion 147 having a second cross sectional area. The first cross sectional area may be less than the second cross sectional area. The top portion 145 of the upper housing 140 may include an upper exterior surface 142, which may be configured to be received in the cap 110 and overlap with at least a portion of the inner peripheral surface 112 of the cap 110.

The bottom portion 147 of the upper housing 140 may define a rim 143, which may define a transition from the first cross sectional area of the top portion 145 to the second cross section area of the bottom portion 147. The edge 113 of the cap 110 may abut the rim 143 when the cap 110 is attached to or installed on the upper housing 140. The interface between the edge 113 and the rim 143 may define the seal 127, as shown in FIG. 1A.

The top portion 145 of the upper housing 140 may define one or more recesses 144, which may be configured to receive the one or more clips or protrusions 114 on the cap 110. The coupling of the one or more recesses 144 with the one or more clips or protrusions 114 may further prevent or inhibit the cap 110 from detaching from the upper housing 140.

The upper housing 140 may also include a top surface 149, which may define one or more orifices 146. The one or more orifices 146 may accept a slider 116 that may be slidably mounted within the electronics module 105. It will be appreciated that having more than one orifice 146 may permit the upper housing 140 and/or the cap 110 to be rotated axially 180 degrees without affecting the manner in which they are attached to one another. In other words, the slider 116 may still be received by at least one of the orifices 146 if the upper housing 140 and/or the cap 110 are rotated axially by 180 degrees.

The inhaler 100 may include a yoke 170, which may be housed within the upper housing 140. The yoke 170 may be cylindrical and may define a hollow portion therein. The yoke 170 may house a bellows (e.g., the bellows 180 shown in FIG. 1D), for example, within the hollow portion. A top surface 172 of the yoke 170 may include one or more apertures 174. The yoke 170 may be mechanically coupled to the mouthpiece cover 130 such that the yoke 170 may move axially along an axis 176 when the mouthpiece cover 130 is moved between the open and closed positions. For example, the yoke 170 may be mechanically coupled to the mouthpiece cover 130 via the hinge mechanism 160. The yoke 170 may be mechanically coupled to the mouthpiece cover 130 via cam followers 178 that extend within the lower housing 150 on either side of the mouthpiece 120 from the hinge mechanism 160 to a belt 179 that is distal from the hinge mechanism 160. The belt 179 may be housed within the lower housing 150. The belt 179 may be configured to engage a bottom edge 171 defined by the yoke 170 such that the cam followers 178 are mechanically coupled to the yoke 170. The cam followers 178 may be configured to engage respective cams 162 of the hinge mechanism 160 of the mouthpiece cover 130. When the mouthpiece cover 130 is opened, the cams 162 of the hinge mechanism 160 may rotate causing the cam followers 178 to move along the axis 176 such that the yoke 170 may move along the axis 176 in a direction towards the lower housing 150. The movement of the yoke 170 along the axis 176 may cause the bellows to compress, resulting in a dose of medicament being transferred to a dose cup (not shown) within the lower housing 150.

As noted above, the electronics module 105 may include components for monitoring parameters associated with the usage and operation of the inhaler 100. For example, the electronics module 105 may include a pressure sensor (not shown) for sensing pressure changes within the housing 190 (more particularly, within the cap 110) resulting from a patient's inhalation or exhalation at the mouthpiece 120. A negative change in pressure may be indicative of an inhalation while a positive change in pressure may be indicative of an exhalation. The electronics module 105 may correlate the measured pressure changes with an air flow rate through the air flow path 189. For example, the electronics module 105 may determine an air flow rate resulting from a patient's inhalation or exhalation at the mouthpiece 120. The determined air flow rate may represent an average air flow rate over the duration of the inhalation or exhalation. The determined air flow rate may also represent a peak air flow rate. The determined air flow rate may be indicative of the quality of the patient's inhalation. That is, a higher flow rate may be generally associated with a stronger inhalation, which may increase the likelihood that a full dose of medicament will be delivered to the patient's lungs. Conversely, a lower flow rate may be generally associated with a weaker inhalation, which may decrease the likelihood that a full dose of medicament will be delivered to the patient's lungs. Accordingly, by determining and tracking the air flow rate through the air flow path 189 during each use of the inhaler 100, the electronics module 105 may be configured to generate adherence and compliance data that may be useful to patients and other third parties, such as healthcare providers.

The seal 127 (e.g., mechanical interface) between the cap 110 and the upper housing 140 may be configured to enable the electronics module 105 to properly measure and/or sense inhaler operation properties and/or statistics. For example, a length of the overlap between the upper exterior surface 142 of the upper housing 140 and the inner peripheral surface 112 of the cap 110 may be configured such that a sufficient air seal is maintained at the seal 127 between the cap 110 and the upper housing 140. In particular, the air seal may be sufficient to permit a pressure sensor in the electronics module 105 to sense pressure changes within the housing 190 (more particularly, within the cap 110) resulting from a patient's inhalation at the opening 122 of the mouthpiece 120 and to enable the electronics module 105 to properly correlate such pressure changes with an air flow rate through air flow path 189 of the inhaler 100. If the seal 127 is poor and an excessive amount of ambient air is allowed to enter the through the seal 127, the inhalation at the opening 122 may result in a lower-than-expected pressure change. Accordingly, in such cases, any pressure change detected by the pressure sensor may not accurately reflect the actual air flow rate through the air flow path 189.

Figure 1C:
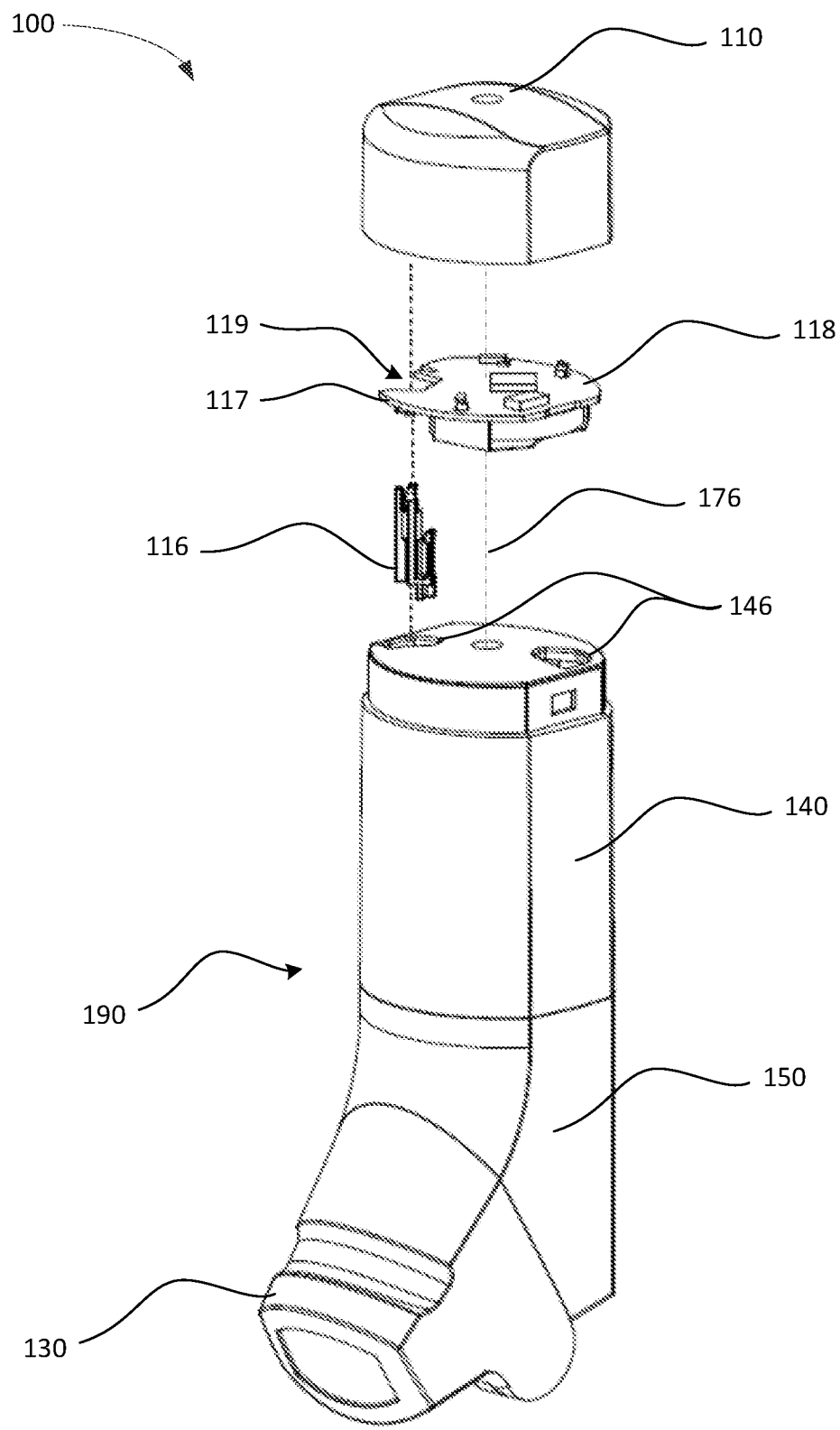
FIG. 1C shows a partially-exploded view of an example inhaler with an electronics module.
Figure 1D:
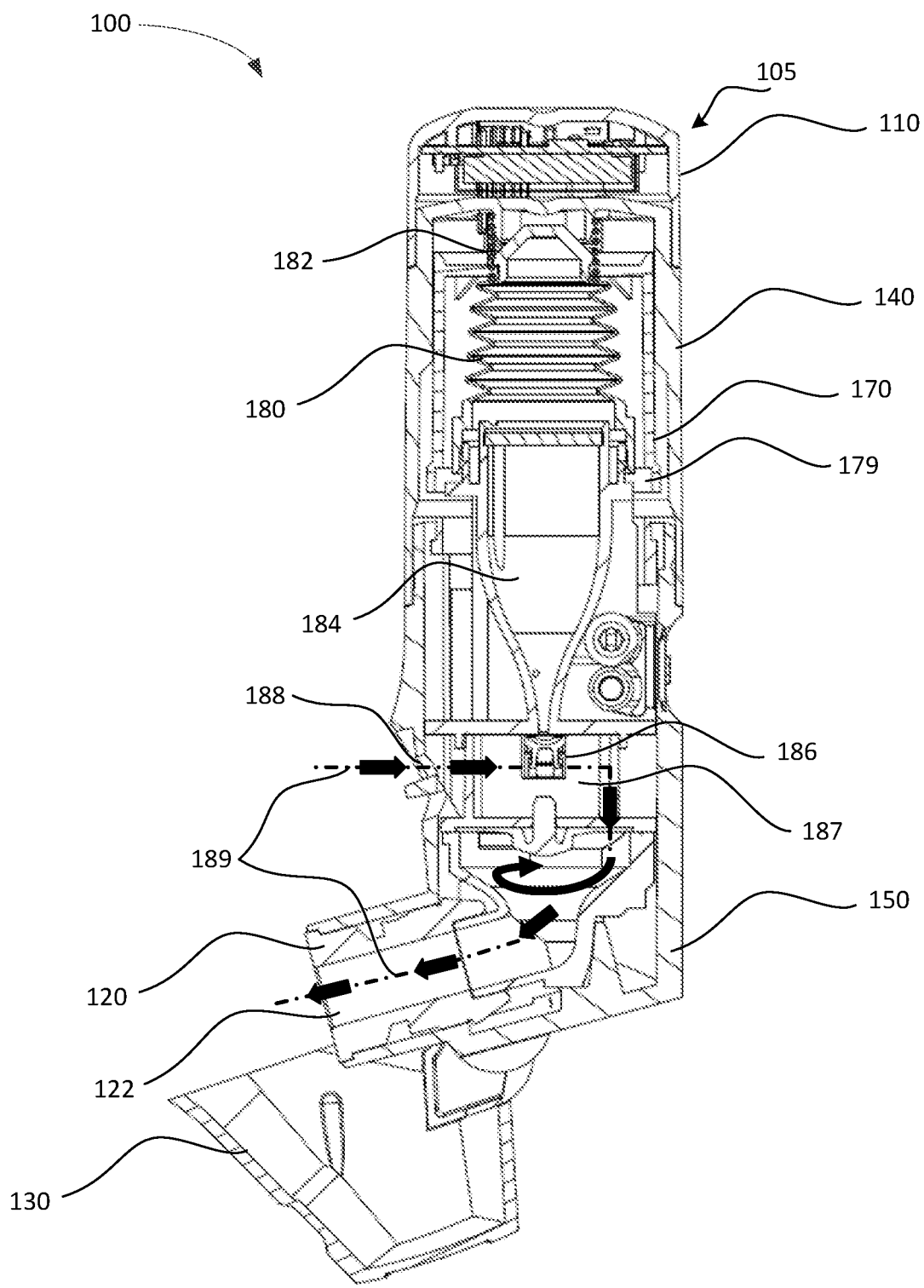
FIG. 1D shows a cross-section view of an example inhaler with an electronics module.

FIG. 1C depicts another partially exploded view of the inhaler 100. As shown, the cap 110 of the electronics module 105 may house a printed circuit board (PCB) 118, which may have an edge 117 that defines a notch 119. The PCB 118 may be attached to the cap 110 via a plurality of heat stakes, as further described herein. The heat stakes may be configured to retain the PCB 118 within the cap 110 and/or meet a drop test requirement without the use of fasteners, for example. The slider 116 may mechanically couple the PCB 118 to the operation of the mouthpiece cover 130. For example, the slider 116 may move axially to activate a switch (e.g., the switch 222 shown in FIGS. 2A and 2B) on the PCB 118 when the mouthpiece cover 130 is opened to expose the mouthpiece 120.

When the slider 116 is slidably mounted within the electronics module 105, a first (e.g., upper) portion of the slider 116 may protrude through the notch 119. A second (lower) portion of the slider 116 may protrude through one of the orifices 146 and extend into the upper housing 140. As discussed further herein, a slider spring (e.g., the slider spring 260 shown in FIG. 2B) within the electronics module 105 may bias the slider 116 in a downward direction, i.e., push the slider towards the lower housing 150. As such, the slider spring may cause the end of the slider 116 within the upper housing 140 to maintain contact with, and continually rest against, the top surface 172 of the yoke 170. Thus, the slider 116 may move axially with the yoke 170 along the axis 176 when the mouthpiece cover 130 is moved between the open and closed positions.

FIG. 1D is a cross-sectional view of the inhaler 100. The inhaler 100 may have an activation spring 182 disposed in the upper housing 140 and a bellows 180 disposed within the yoke 170. The activation spring 182 may bias the yoke 170 against the bellows 180. When the mouthpiece cover 130 is opened to expose the mouthpiece 120, the yoke 170 may move axially in a direction towards the lower housing 150. The bias against the yoke 170 from the activation spring 182 may cause the bellows 180 to compress, thereby resulting in a dose of medicament being transferred from a reservoir 184 to a dose cup 186 in the lower housing 150. As noted above, the inhaler 100 may be a breath-actuated DPI. Thus, the inhaler 100 may include a deagglomerator 187, which may be configured to aerosolize the dose of medicament by breaking down the agglomerates of the medicament in the dose cup 186 when the air flow through the air flow path 189 meets or exceeds a particular rate, or is within a specific range. When aerosolized, the dose of medicament may be delivered orally to a patient via the air flow path 189 extending through the mouthpiece 120.

The air flow path 189 may be a medicament delivery air flow path that extends from the opening 122 on the mouthpiece 120 through the deagglomerator 187 and through a vent 188 on the lower housing 150. The vent 188 may serve as the inlet for air flow path 189. The opening 122 on the mouthpiece 120 may serve as the outlet for the air flow path 189. The medicament may be introduced into the air flow path 189 when the patient breathes-in or inhales. For example, when the patient breathes-in or inhales from the mouthpiece 120, air is pulled through the vent 188 to the deagglomerator 187. The air is then pulled through the deagglomerator 187 where the air mixes with the medicament. The air-medicament mixture may exit the inhaler 100 via the opening 122 of the mouthpiece 120.

The seal 127 between the cap 110 and the upper housing 140 may be configured such that medication delivery is not adversely affected. For example, the deagglomerator 187 may be configured to aerosolize a dose of medicament from the reservoir 184 when the air flow rate via the air flow path 189 reaches or exceeds 30 LPM or, more preferably, when the air flow rate reaches or exceeds 45 LPM. Thus, the inhaler 100 may be configured to yield a particular air flow rate through the air flow path 189 when a certain pressure is applied at the opening 122 of the mouthpiece 120. The relationship between the air flow rate and applied pressure may change if there are undesirable gaps or openings in the housing 190. That is, a higher pressure (e.g., a stronger inhalation) at the opening 122 may be required if the air flow resistance associated with the air flow path 189 has changed (e.g., decreased) due to excessive ambient air entering the housing 190 through the seal 127. This increased pressure (or stronger inhalation) may be beyond the physical capabilities of patients with limited lung function. Accordingly, the sufficiency of the seal 127 between the upper housing 140 and the cap 110 may affect the ability of the inhaler 100 to deliver a proper dose of medicament.

In view of the foregoing, the mechanical interface between the cap 110 and the upper housing 140 may be configured such that, at a given pressure applied at the opening 122, the air flow rate through the air flow path 189 of the inhaler 100 may be substantially similar to the air flow rate through the air flow path 189 of an inhaler 100 without the electronics module 105 and/or where the top portion 145 of the upper housing 140 does not include any openings, such as orifices 146). Preferably, at a given applied pressure, the air flow rates may be within 2% of one another.

Moreover, a suitable air flow resistance associated with the air flow path 189 of the inhaler 100 may fall within the range of 0.020 kilopascal per liters per minute ($kPa^{0.5}$/LPM) to 0.042 $kPa^{0.5}$/LPM. More preferably, the air flow resistance associated with the air flow path 189 of the inhaler 100 may fall within the range of 0.025 $kPa^{0.5}$/LPM to 0.037 $kPa^{0.5}$/LPM. Even more preferably, the air flow resistance associated with the air flow path 189 of the inhaler 100 may fall within the range of 0.028 $kPa^{0.5}$/LPM to 0.034 $kPa^{0.5}$/LPM.

A suitable air flow rate associated with the air flow path 189 of the inhaler 100 may fall within the range of 50 LPM to 80 LPM when a pressure drop of 4.0 kPa is applied across the air flow path 189. More preferably, the air flow rate associated with the air flow path 189 of the inhaler 100 may fall within a range of 55 LPM to 75 LPM when a pressure drop of 4.0 kPa is applied across the air flow path 189. Even more preferably, the air flow rate associated with the air flow path 189 of the inhaler 100 may fall within a range of 59 LPM to 71 LPM when a pressure drop of 4.0 kPa is applied across the air flow path 189.

Figure 2A:
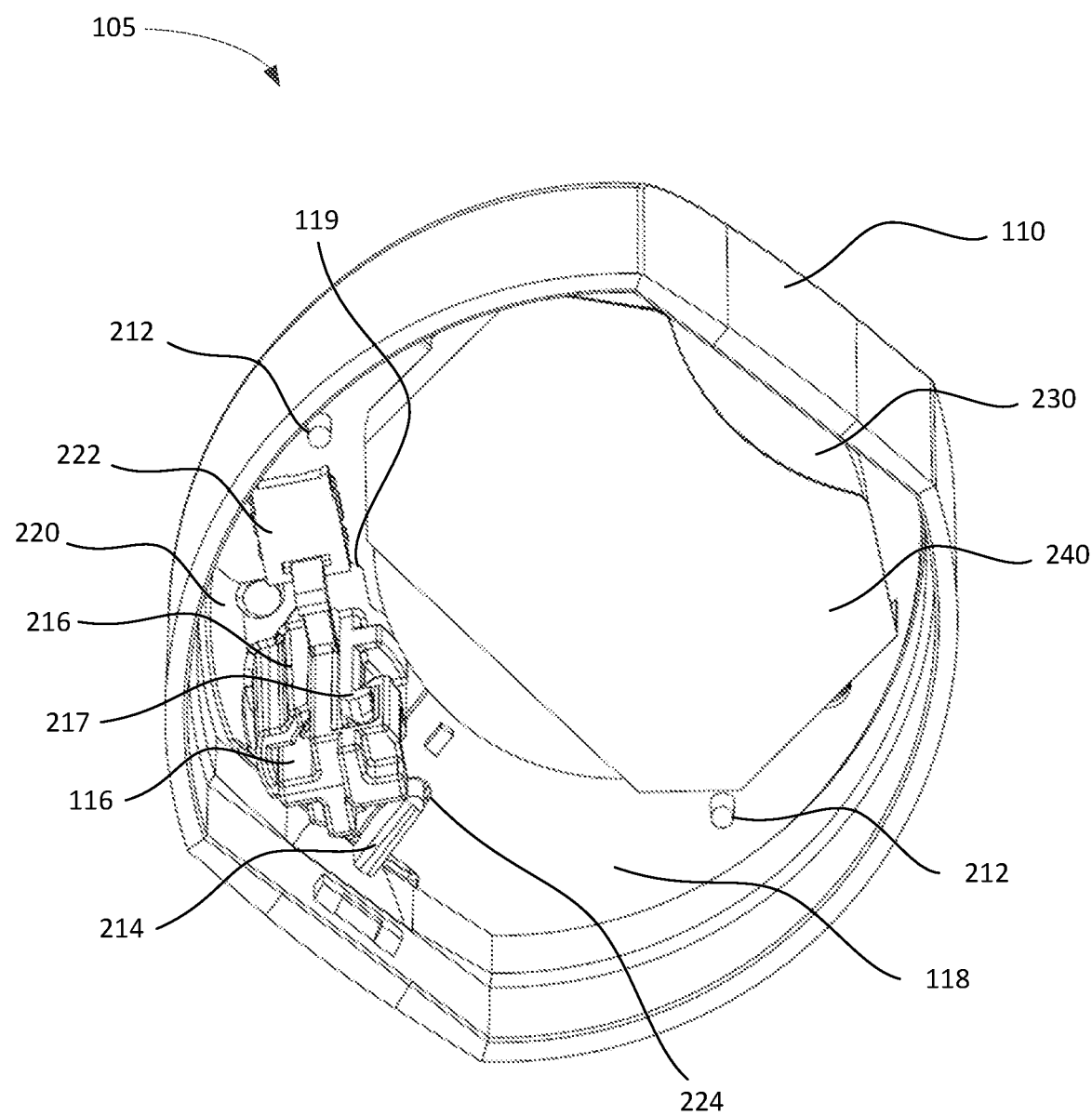
FIG. 2A depicts an example electronics module for an inhaler.
Figure 2B:
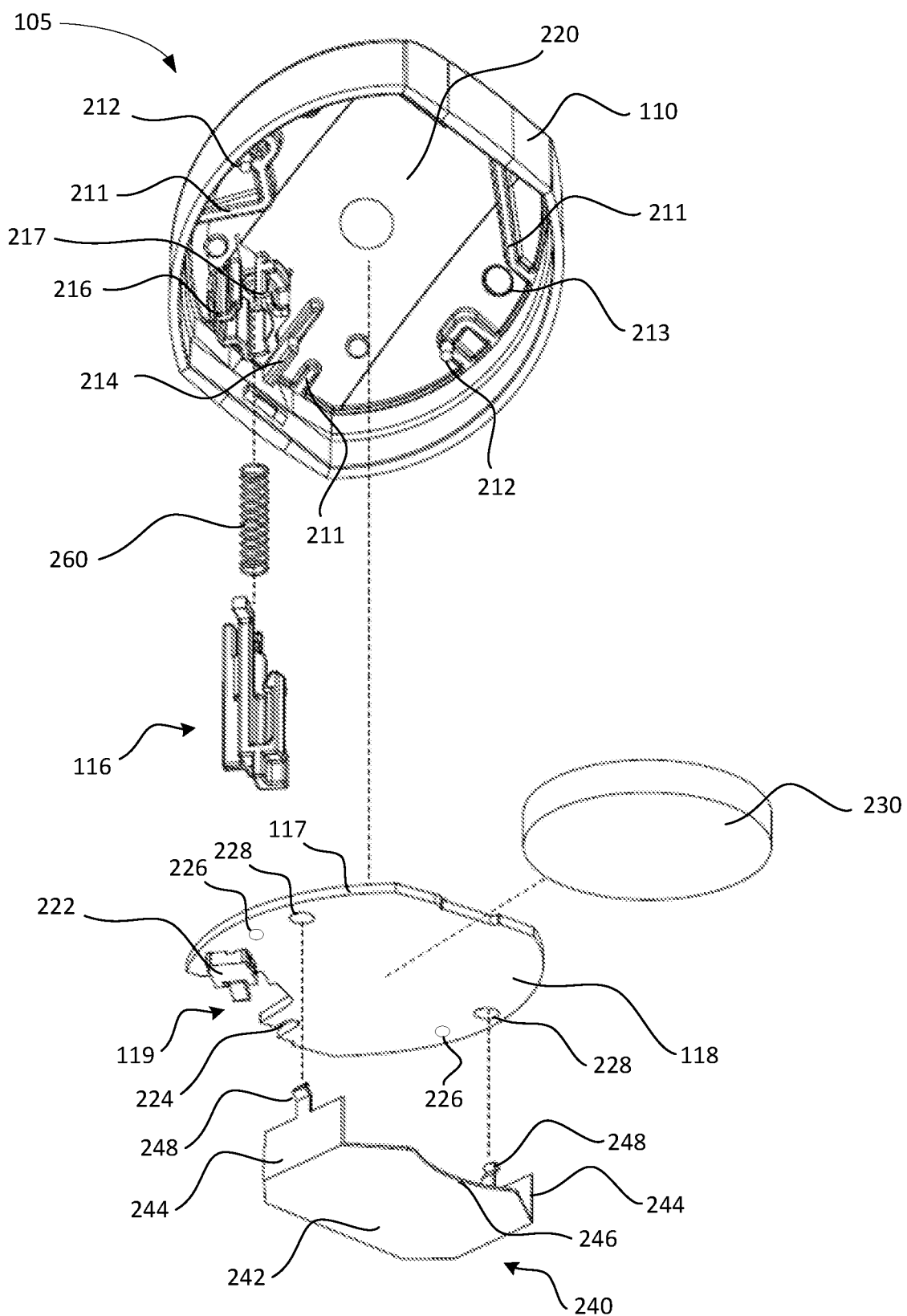
FIG. 2B shows a partially-exploded view of an example electronics module for an inhaler.

FIG. 2A depicts the exemplary electronics module 105 for the inhaler 100. FIG. 2B shows a partially-exploded view of the exemplary electronics module 105 for the inhaler 100. The electronics module 105 may include a cap 110, a PCB 118, a battery 230, a battery holder 240, and a slider 116. The PCB 118 may be mounted within the cap 110.

Respiratory devices, such as the inhaler 100, may be required to successfully pass a drop test. The drop test may involve dropping the respiratory device from a predetermined height to assess the extent to which the device's operation and/or performance are adversely impacted. Fastening the PCB 118 to the cap 110 using fasteners (e.g., screws, rivets, etc.) may result in failure of the drop test. For example, the operation and/or performance of the inhaler 100 may be adversely impacted when the PCB 118 is attached to the cap 110 using fasteners. Using fasteners to fasten the PCB 118 to the cap 110 may also increase manufacturing cost and/or manufacturing time. As such, the cap 110 may include a plurality of heat stakes, such as heat stakes 212, 214.

The heat stakes 212, 214 may be configured to secure the PCB 118 to the cap 110, for example, without the use of fasteners. The heat stakes 212, 214 may protrude or extend from a top inner surface 220 of the cap 110. The heat stakes 212 may have a circular cross section. The heat stakes 212 may have a diameter that is smaller than a standard heat stake diameter. That is, the diameter of the heat stakes 212 may be selected such that the inhaler 100 will successfully pass the drop test without taking up too much space on the PCB 118. Preferably, the heat stakes 212 may have a diameter less than 1.4 mm. The PCB 118 may have a plurality of openings 224, 226, 228, as shown in FIG. 2B. One or more of the openings (e.g., the openings 226) may correspond to the heat stakes 212 such that the heat stakes 212 may be adapted to protrude through the PCB 118 via the openings 226 when the PCB 118 is mounted within the cap 110.

The heat stake 214 may have a non-circular cross-section, for example, such as a rib-shaped cross-section. The plurality of openings on the PCB 118 may include a notch 224 that corresponds to the location of the heat stake 214, for example. The PCB 118 may define the notch 224 such that the heat stake 214 may be adapted to protrude through the PCB 118 via the notch 224 when the PCB 118 is mounted within the cap 110. Each of the heat stakes 212 and the heat stake 214 may define a distal end that is opposite from the top inner surface 220 of the cap 110. The distal end of each of the heat stakes 212 and the heat stake 214 may be configured to be partially deformed when heated to a predetermined temperature. The partially deformed heat stakes 212 and heat stake 214 may secure the PCB 118 to the cap 110.

The PCB 118 may include a switch 222, which may be a toggle switch or a detector switch. The arm of a detector switch may have a range of motion, or larger tolerance, than the range of motion on a toggle switch. As such, a detector switch may have a lower risk of damage when engaged/disengaged by the slider 116. The switch 222 may provide a wake signal to the electronics module 105, for example, when activated. The wake signal may transition the electronics module 105 from a first operational state to a second operational state. The first operational state may be an off state or a sleep state. The second operational state may be an active (e.g., on) state.

The electronics module 105, being installed at the top of the inhaler (e.g., distal from the mouthpiece 120), may include an adapter device to mechanically engage the switch 222 as the mouthpiece cover 130 is opened and/or closed. For example, the slider 116 may be configured to activate the switch 222. The switch 222 may be located adjacent to the notch 119, for example, such that the slider 116 activates and deactivates the switch 222 as it moves axially. As described herein, the slider 116 may move axially when the mouthpiece cover 130 is opened and closed.

The cap 110 may include a slider guide 216. The slider guide 216 may protrude from the top inner surface 220 of the cap 110. The slider guide 216 may be configured to accept the slider 116 such that the slider is slidably mounted within the cap 110. For example, the slider guide 216 may be configured to accept a portion of the slider 116. The slider guide 216 may define a stopper 217. The stopper 217 may be configured to retain the slider 116 within the slider guide 216. The stopper 217 may be further configured to limit an axial travel of the slider 116, for example, when the mouthpiece cover 130 is opened and/or closed.

The cap 110 may define a plurality of datum ribs 211. The datum ribs 211 may be configured to support the PCB 118. The datum ribs 211 may be configured to locate the PCB 118 a predetermined distance from the top inner surface 220 of the cap 110. The datum ribs 211 may be any shape and may be configured to allow for clearance of electrical components mounted to the PCB 118. The cap 110 may define a plurality of recesses 213. The recesses 213 may be cavities in the top inner surface 220 of the cap 110. The recesses 213 may be configured to allow for clearance of one or more electrical components mounted to the PCB 118. For example, the recesses 213 may accept respective portions of the one or more electrical components mounted to the PCB 118.

The PCB 118 may further include a processor and a transmitter. The PCB 118 may be installed towards the end of manufacture of the inhaler (e.g., following equilibration of the inhaler). Installing the PCB 118 towards the end of the manufacture of the inhaler 100 may be advantageous since equilibration of the inhaler 100 may damage the sensitive electronics on the PCB 118. Equilibration may involve filing the inhaler 100 with a medicament and storing the inhaler 100 at a predefined temperature and humidity for duration of time (e.g., four weeks) before final packing of the inhaler 100.

The battery holder 240 may be a through hole type battery holder. For example, the battery holder 240 may define a base 242 and two legs 244. The length of the legs 244 may be configured such that the battery holder 240 can accept the battery 230. The base 242 may include a curved edge 246. The curved edge 246 may be configured to allow access to the battery 230. The battery holder 240 may have tabs 248 that extend from the legs 244. The tabs 248 may extend from the legs 244 substantially perpendicular to the base 242. The tabs 248 may be configured to attach the battery holder 240 to the PCB 118. For example, the tabs 248 may extend through openings 228 defined by the PCB 118. The tabs 248 may be compliant such that the tabs deflect and engage the openings 228 such that the battery holder 240 is removably attached to the PCB 118.

The battery holder 240 may be configured such that the battery 230 maintains contact with the PCB 118. The battery holder 240 may be secured to the PCB 118. The battery holder 240 may be configured such that an electrical connection may be formed between the PCB 118 and the battery 230 (e.g., such as a coin cell). One or more components of the PCB 118 may be selectively activated based on a position of the mouthpiece cover 130. For example, activation of the switch 222 (e.g., or activation of some other switching means, such as an optical sensor, an accelerometer, or a Hall effect sensor) may wake a processor and/or transmitter from an off state (or a power-conserving sleep mode) to an on state (or an active mode). Conversely, deactivation of the switch 222 may transition the processor and/or transmitter from the on state (or active mode) to an off state or a lower power mode.

As noted above, the PCB 118 may include a sensor (not shown) that may provide information to the processor about a patient's inhalation. The sensor may be a pressure sensor, such as a MEMS or NEMS pressure sensor (e.g., a barometric pressure sensor, a differential pressure sensor, etc.). The sensor may provide the information for example, using a pressure change and/or a pressure difference. The sensor may provide an instantaneous pressure reading to the processor and/or aggregated pressure readings over time. The processor may use the information to determine an air flow rate associated with the patient's inhalation through the air flow path 189. The processor may also use the information to determine the direction of air flow. That is, a negative change in air pressure through the air flow path 189 may indicate that the patient has inhaled from the mouthpiece 120 while a positive change in air pressure through the air flow path 189 may indicate that the patient has exhaled into the mouthpiece 120.

The electronics module 105 may further include a wireless communication circuit, such as a Bluetooth chipset (e.g., a Bluetooth Low Energy chipset). As such, the electronics module 105 may provide a pressure measurement to an external device (e.g., a smartphone), which may perform additional calculations on the pressure measurement data, provide feedback to the user, and/or the like. The electronics module 105 may include a control circuit, which for example, may be part of the communication circuit.

Based on the information or signals received from the switch 222 and/or the sensor, the electronics module 105 may determine whether the mouthpiece cover 130 has been open or closed and whether a received pressure measurement exceeds a threshold or is within a specific pressure range, which may be indicative of whether the medication inhaled by a user has reached a predetermined or prescribed level. The pressure measurement threshold(s) and/or range(s) may be stored in a memory of the electronics module 105. When the predetermined threshold or range is met, the electronics module 105 may determine the state of the inhaler 100 and may generate a signal that indicates the state of the inhaler 100.

The electronics module 105 may include a memory (not shown) for storing data collected by the sensor (e.g., pressure measurements) and/or data generated by the processor (e.g., air flow rates). The stored data may be accessed by the processor and wirelessly communicated to an external device, such as a smartphone, via the wireless communication circuit. The memory may be non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The electronics module 105 may access information from, and store data in, a memory that is not physically located within the inhaler 100, such as on a server or a smartphone.

The processor of the electronics module 105 may comprise a microcontroller, a programmable logic device (PLD), a microprocessor, an application specific integrated circuit (ASIC), a field-programmable gate array (FPGA), or any suitable processing device, controller, or control circuit. The processor may comprise an internal memory.

The processor of the electronics module 105 may receive power from the battery 230, and may be configured to distribute and/or control the power to the other components in the electronics module 105. The battery 230 may be any suitable device for powering the electronics module 105. The battery 230 may be directly connected to one or more of the sensor, the memory, and/or the transceiver of the electronics module 105.

Figure 3:
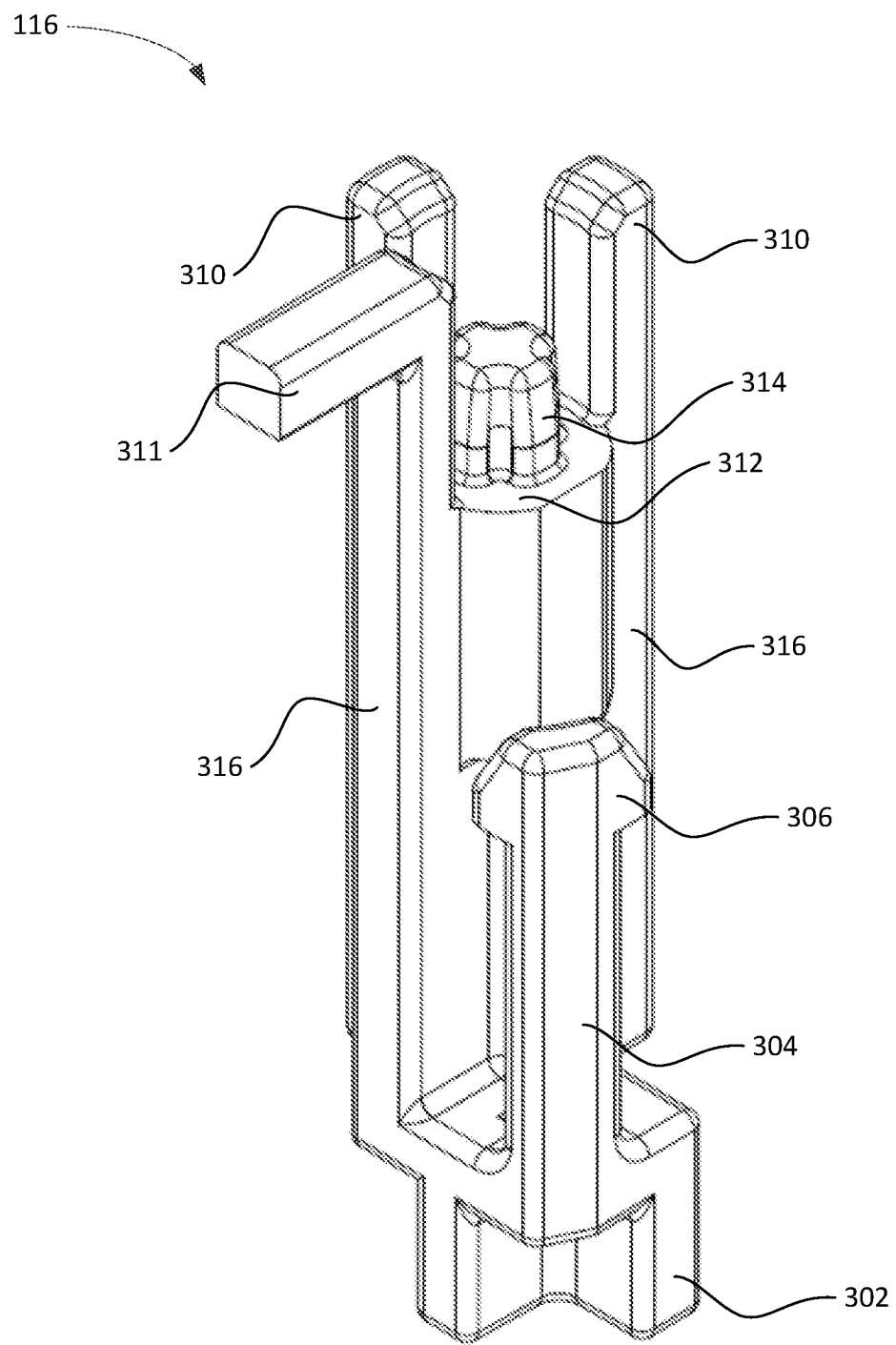
FIG. 3 depicts an example slider of an electronics module for an inhaler.

FIG. 3 illustrates the example slider 116 for the inhaler 100. As described herein, the slider 116 may be mechanically coupled to the mouthpiece cover 130 of the inhaler such that the slider 116 engages a switch 222 in the electronics module 105 as the mouthpiece cover 130 is opened and/or closed. The slider 116 may include a distal end 302 (e.g., a base). The slider 116 may include an arm 304. The arm 304 may extend from the distal end 302. The arm 304 may define a clip 306. The clip 306 may be an enlarged section of the arm 304. The clip 306 may be configured to engage the stopper 217, shown in FIGS. 2A and 2B. The arm 304 may be compliant about its connection with the slider 116. For example, the arm 304 may be configured to flex towards and/or away from the slider 116 in response to an applied force. The clip 306 may have an inclined surface such that the arm 304 flexes away from the slider 116 (e.g., until the clip 306 engages the stopper 217) when the slider 116 is pressed into the slider guide 216, shown in FIGS. 2A and 2B.

The slider 116 may define a spring seat 312. The spring seat 312 may be an upper horizontal surface of the slider 116. A spring cruciform 314 may extend from the spring seat 312. The spring cruciform 314 may be configured to extend within and captively engage a slider spring 260 (shown in FIG. 2B). The slider 116 may define one or more ribs 316. The ribs 316 may define one or more fingers 308, 310 that extend beyond the spring cruciform 314. The finger 308 may be configured to engage the switch 222 of the inhaler 100. For example, the finger 308 may include a horizontal extension 311. The horizontal extension 311 may extend in a direction opposite the spring cruciform 314. One or more fingers 310 may be configured to limit vertical travel of the slider 116. For example, the fingers 310 may abut a surface in the slider guide 216 (shown in FIGS. 2A and 2B) when the slider spring 260 is compressed.

FIGS. 4A-4B are projection views of the example slider 116. The ribs 316 may be rectangular protrusions that extend along the length of the slider 116. The ribs 316 may be configured to engage (e.g., abut) inside surfaces of the slider guide 216 such that the slider 116 remains aligned within the slider guide 216. The slider 116 may define an intermediate surface 303. The ribs 316 may extend from the intermediate surface 303. Each of the ribs 316 may include one of fingers 308, 310. For example, one of the ribs 316 may define the finger 308. The distal end 302 of the slider 116 may be offset from the finger 308. The finger 308 may define a centerline 309. The distal end 302 of the slider 116 may be offset a distance D1 from the centerline 309. The distal end 302 of the slider 116 may extend from the intermediate surface 303. The distal end 302 of the slider 116 may define a bottom surface 301. The bottom surface 301 may be configured to abut the yoke 170 of the inhaler 100. The bottom surface 301 may extend a distance D2 from the intermediate surface 303. For example, the distance D2 may be about 2.0 mm (e.g., 2.0 mm with a manufacturing tolerance of approximately +/−0.1 mm).

The slider 116 may define a spring seat 312 and a spring cruciform 314. The spring cruciform 314 may extend a distance D3 from the spring seat 312. For example, the distance D3 may be about 1.5 mm (e.g., 1.5 mm with a manufacturing tolerance of approximately +/−0.1 mm).

The arm 304 of the slider 116 may include a clip 306. The clip 306 may be an enlarged section of the arm 304 that is configured as a stopping mechanism. For example, the clip 306 may define a stopper surface 305. The stopper surface 305 may be configured to abut a stopper, such as the stopper 217 of the slider guide 216 of the cap 110, as shown in FIGS. 2A and 2B. The finger 308 may include a horizontal extension 311 that may extend orthogonally from the corresponding rib of the ribs 316. For example, the horizontal extension 311 may extend a distance D4 from the corresponding rib of the ribs 316. The distance D4 may be configured such that the horizontal extension 311 engages the switch 222 of the PCB 118 (e.g., as shown in FIGS. 5A-5D) without obstructing the travel of the slider 116. For example, the distance D4 may be about 2.30 mm (e.g., 2.30 mm with a manufacturing tolerance of approximately +/−0.07 mm). The finger 308 may define a top surface 307. For example, the top surface 307 may be defined by the horizontal extension 311. The stopper surface 305 may be a distance D5 from the top surface 307. The distance D5 may be configured to limit the vertical travel of the slider 116 within the slider guide 216. For example, the distance D5 may be configured to limit the vertical travel of the slider 116 after the slider 116 activates the switch 222 on the PCB 118 of the electronics module 105. For example, the distance D5 may be about 7.22 mm (e.g., 7.22 mm with a manufacturing tolerance of approximately +/−0.09 mm). The top surface 307 may be a distance D6 from the spring seat 312. For example, the distance D6 may be about 3.52 mm (e.g., 3.52 mm with a manufacturing tolerance of approximately +/−0.1 mm).

The slider 116 may define one or more second fingers 310. For example, one or more of the ribs 316 may define the second fingers 310. The second fingers 310 may extend a distance D7 from the spring seat 312. For example, the distance D7 may be about 3.12 mm (e.g., 3.12 mm with a manufacturing tolerance of approximately +/−0.1 mm).

FIGS. 5A-5D illustrate operation of the slider 116 of the example inhaler 100 as the mouthpiece cover 130 is operated from a closed position to an open position (e.g., a partially open position). In particular, movement of the mouthpiece cover 130 from the closed position to the open position may cause the slider 116 to travel axially, in a downward direction towards the mouthpiece 120. As the slider 116 moves in the downward direction, a portion of the slider 116 may physically engage with, and thus activate, the switch 222. Conversely, movement of the mouthpiece cover 130 from the open position to the closed position may cause the slider 116 to travel in an upward direction towards the cap 110. As the slider 116 moves in the upward direction, the portion of the slider 116 may physically disengage with, and thus deactivate, the switch 222.

More specifically, the yoke 170 may be configured to move up and down within the upper housing 140 of the inhaler 100 when the mouthpiece cover 130 is opened and closed. The slider 116 may be operably coupled to the mouthpiece cover 130 via the yoke 170. The up and down movement of the yoke 170 may cause the slider 116 to activate and/or deactivate, respectively, the switch 222. For purposes of simplicity, the mouthpiece cover 130 is illustrated in four positions, a closed position in FIG. 5A, a first position in FIG. 5B, a second position in FIG. 5C, and a third position in FIG. 5D. However, it should be noted that when opening the mouthpiece cover 130, the mouthpiece cover 130 may transition between any number of distinct positions as the mouthpiece cover 130 is transitioned from the closed position to a fully open position, and vice versa.

Figure 5A:
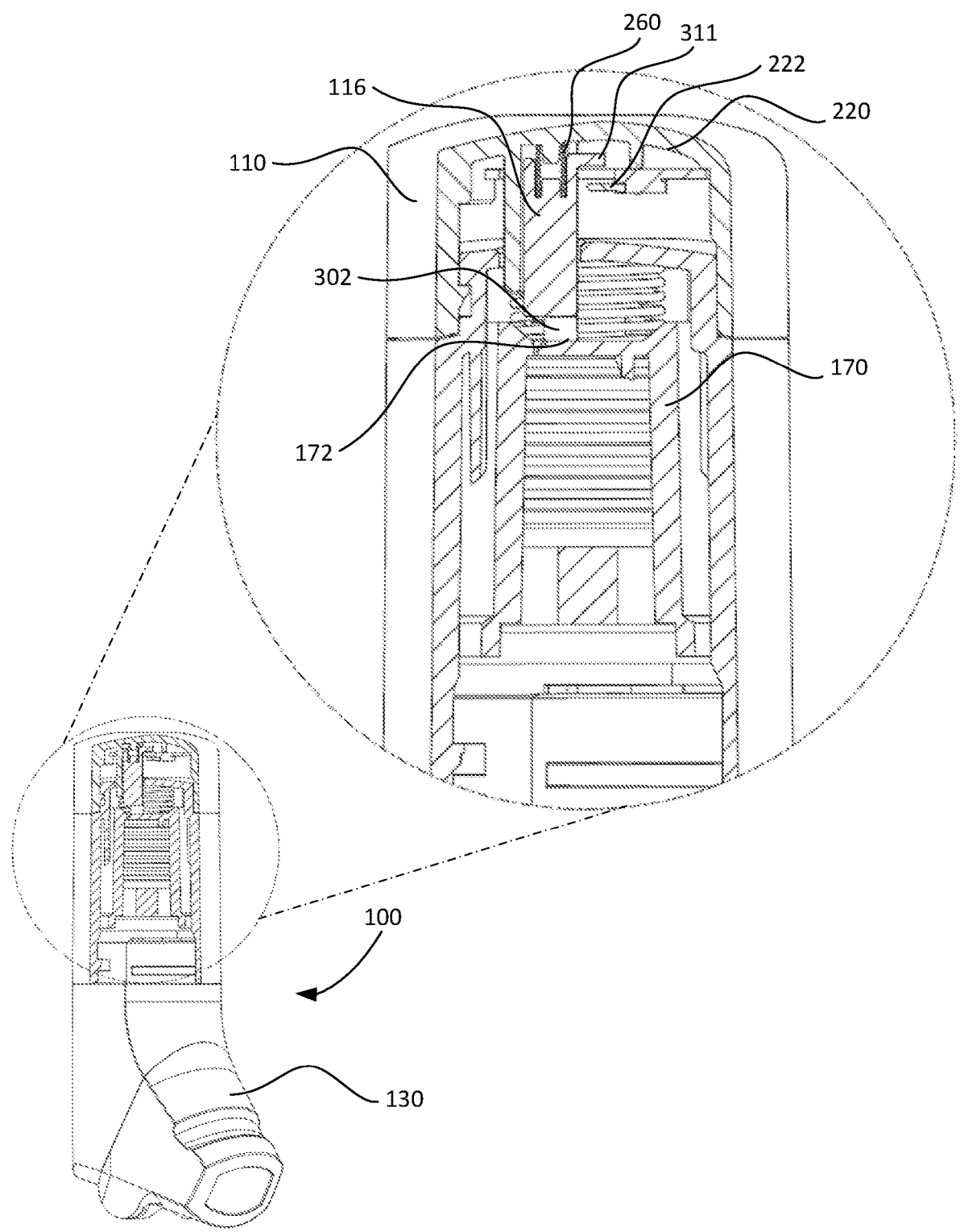
FIGS. 5A-D illustrate operation of an example slider in an inhaler.

As shown in FIG. 5A, the slider 116 may be in an intermediate position when the mouthpiece cover 130 is in the closed position. When the slider 116 is in the intermediate position, the horizontal extension 311 of the slider 116 may be located between the top inner surface 220 of the cap 110 and the switch 222. The slider spring 260 may be partially compressed when the slider 116 is in the intermediate position. The distal end 302 of the slider 116 may be in contact with the top surface 172 of the yoke 170.

Figure 5B:
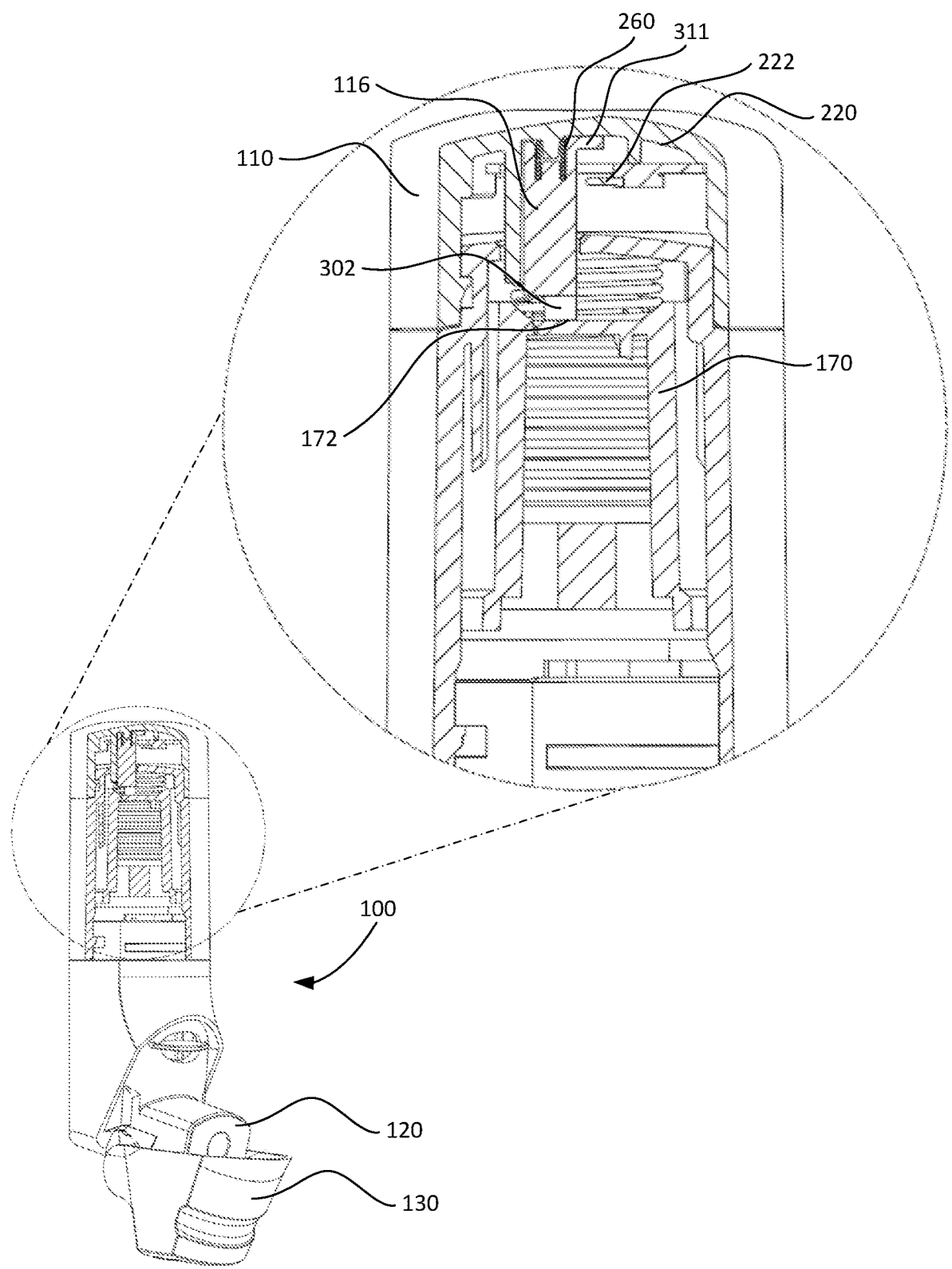

As shown in FIG. 5B, the mouthpiece cover 130 may be opened to the first position. The first position may be a partially open position such that a portion of the mouthpiece 120 is exposed. The slider 116 may be in an upper position such that the horizontal extension 311 of the slider 116 may be closer to the top inner surface 220 of the cap 110 when the mouthpiece cover 130 is in the first position. For example, the horizontal extension 311 may be in contact with the top inner surface 220. The slider spring 260 may be further compressed beyond the partially compressed position associated with the intermediate position of the slider 116. When the slider 116 is in the upper position, the distal end 302 of the slider 116 may remain in contact with the top surface 172 of the yoke 170.

Figure 5C:
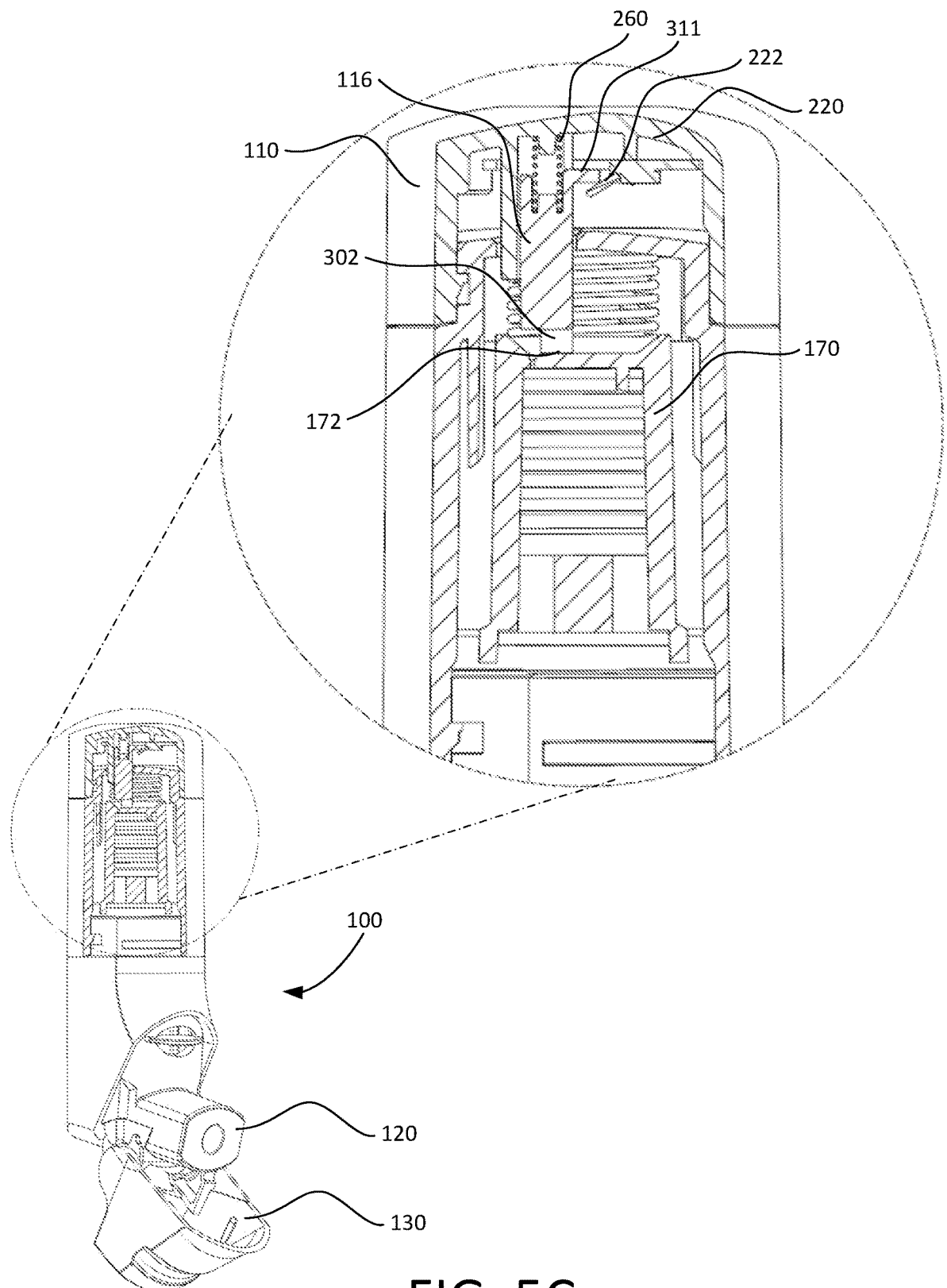

As shown in FIG. 5C, the mouthpiece cover 130 may be opened to the second position. The second position may be a partially open position such that the mouthpiece 120 is more exposed than in the first position. For example, the mouthpiece cover 130 is more open in the second position than in the first position. The slider 116 may be in a contact position such that the horizontal extension 311 of the slider 116 is in contact with the switch 222 when the mouthpiece cover 130 is in the second position. The switch 222 may be activated when the slider 116 is in the contact position. When the slider 116 is in the contact position, the distal end 302 of the slider 116 may remain in contact with the top surface 172 of the yoke 170.

Figure 5D:
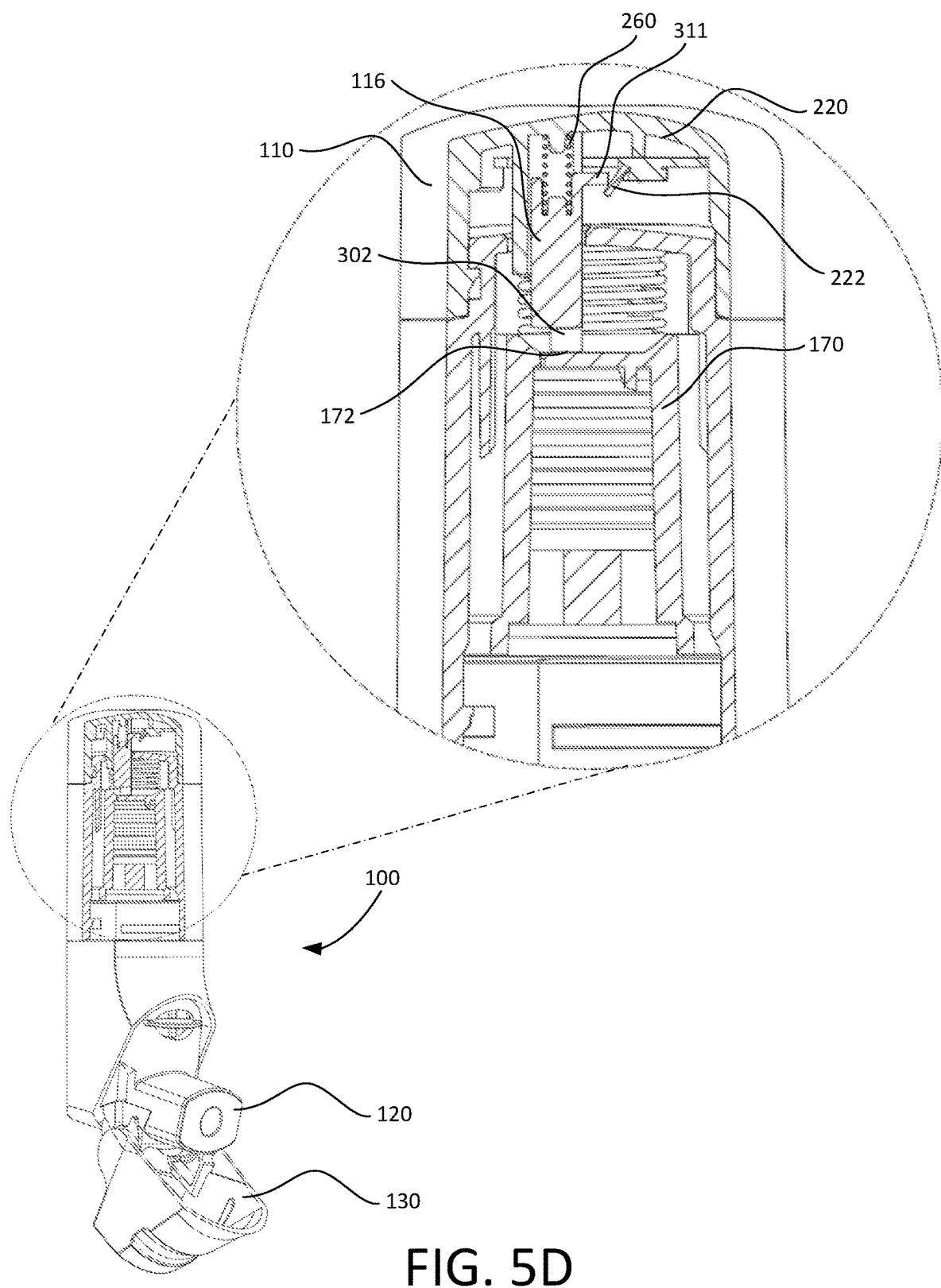

As shown in FIG. 5D, the mouthpiece cover 130 may be opened to the third position. The third position may be a partially open position such that the mouthpiece 120 is more exposed than in the second position. For example, the mouthpiece cover 130 is more open in the third position than in the second position. The horizontal extension 311 of the slider 116 may remain in contact with the switch 222 when the mouthpiece cover 130 is in the third position. The horizontal extension 311 of the slider 116 may activate the switch 222 to a maximum switch travel angle when the mouthpiece cover 130 is in the third position. When the slider 116 is in the activation position, the distal end 302 of the slider 116 may remain in contact with the top surface 172 of the yoke 170.

Figure 6:
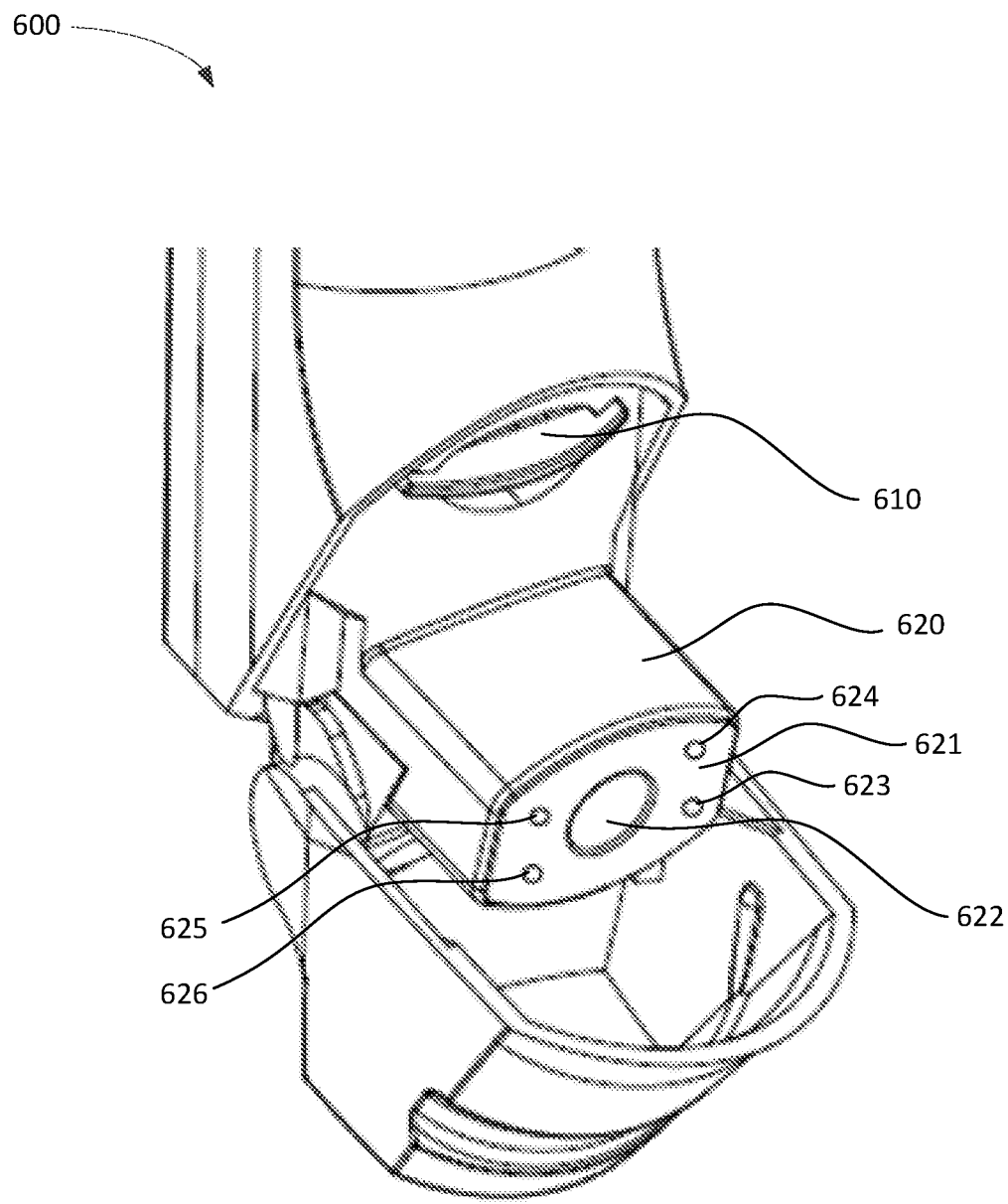
FIG. 6 illustrates an example mouthpiece of an inhaler having a plurality of bypass ports.

FIG. 6 illustrates an example mouthpiece 620 of an inhaler 600 (e.g., such as the example inhaler 100). The example mouthpiece 620 may be an alternate mouthpiece having a plurality of (e.g., four) bypass ports 623, 624, 625, 626. The bypass ports 623, 624, 625, 626 may enable air to flow independent of an air flow path (e.g., such as the air flow path 189 shown in FIG. 1D) such that when a patient breathes-in or inhales through the mouthpiece 620 a portion of the air inhaled by the patient from the air flow path and another portion of the air inhaled by the patient is not from the air flow path. For example, the bypass ports 623, 624, 625, 626 may extend through the mouthpiece 120, exterior to the air flow path, from a front surface 621 of the mouthpiece 620 to a rear surface (not shown) of the mouthpiece 620. The bypass ports 623, 624, 625, 626 may reduce the flow rate through the air flow path to reduce the flow rate dependence of the inhaler 100 and/or to deliver an appropriate dose of medicament at lower flow rates through the air flow path 189.

The mouthpiece 620 may have a front surface 621 that defines a flow path opening 622 and the plurality of bypass ports 623, 624, 625, 626. The flow path opening 622 may be the entrance and/or exit conduit for the air flow path of the inhaler 600. For example, the air flow path may be a breath-actuated air flow path for entraining a dry powder medicament from the inhaler 600 that begins at a vent 610 and ends at the flow path opening 622. The bypass ports 623, 624, 625, 626 may be configured to allow air to flow independently of the air flow path from a region exterior to the mouthpiece 620 to the front surface 621 when a breath induced low pressure is applied to the front surface 621. The bypass ports 623, 624, 625, 626 may reduce the linear flow rate of air through the air flow path and the flow path opening 622. A reduced linear flow rate of air through the flow path opening 622 may reduce fluctuations in the velocity of the air flowing through the air flow path, for example, as a result of changes in breath induced low pressure. That is, the bypass ports 623, 624, 625, 626 may reduce the flow rate dependence of a delivered fine particle dose, e.g., the mass of the active substance below 5 µm. The delivered fine particle dose can be measured according to s. 2.9.18. of the European Pharmacopoeia 6.0 using an Anderson Cascade Impactor.

The bypass ports 623, 624, 625, 626 may reduce the formation of secondary vortices, stalled airflow within a swirl chamber of the airflow path, and/or areas of high sheer on the walls of the swirl chamber, all of which can adversely affect the performance of the inhaler 600.

A ratio of the sum of the bypass ports 623, 624, 625, 626 cross-sectional area to the flow path opening 622 cross-sectional area may be configured such that that when a pressure breath induced low pressure is applied to the front surface 621 of the mouthpiece 620 at least about 5%, preferably at least about 15%, more preferably from about 5% to about 50%, more preferably from about 15% to about 40%, and even more preferably from about 20% to about 30% of the resulting air flow is directed through the bypass ports 623, 624, 625, 626.

For example, the sum of the cross-sectional areas of the bypass ports 623, 624, 625, 626 may be from about 0.75 mm$^2$ to about 20 mm$^2$, more preferably from about 5 mm$^2$ to about 16 mm$^2$, and even more preferably from about 9 mm$^2$ to about 11 mm$^2$.

The flow path opening 622 may have a cross-sectional area of from about 25 mm$^2$ to about 50 mm$^2$, preferably from about 30 mm$^2$ to about 45 mm$^2$, and more preferably from about 35 mm$^2$ to about 45 mm$^2$.

A suitable air flow resistance associated with the air flow path 189 of the inhaler 600 with the electronics module and the bypass ports 623, 624, 625, 626 may fall within the range of 0.015 kPa$^{0.5}$/LPM to 0.031 kPa$^{0.5}$/LPM. More preferably, the air flow resistance associated with the air flow path 189 of the inhaler 600 with the electronics module and the bypass ports 623, 624, 625, 626 may fall within the range of 0.018 kPa$^{0.5}$/LPM to 0.028 kPa$^{0.5}$/LPM. Even more preferably, the air flow resistance associated with the air flow path 189 of the inhaler 600 with the electronics module and the bypass ports 623, 624, 625, 626 may fall within the range of 0.021 kPa$^{0.5}$/LPM to 0.025 kPa$^{0.5}$/LPM.

A suitable air flow rate associated with the air flow path 189 of the inhaler 600 with the electronics module and the bypass ports 623, 624, 625, 626 may fall within the range of 70 LPM to 105 LPM when a pressure drop of 4.0 kPa is applied across the air flow path 189 of the inhaler 600. More preferably, the air flow rate associated with the air flow path 189 of the inhaler 600 with the electronics module and the bypass ports 623, 624, 625, 626 may fall within the range of 75 LPM to 100 LPM when a pressure drop of 4.0 kPa is applied across the air flow path 189. Even more preferably, the air flow rate associated with the air flow path 189 of the inhaler 600 with the electronics module and the bypass ports

623, 624, 625, 626 may fall within the range of 80 LPM to 95 LPM when a pressure drop of 4.0 kPa is applied across the air flow path 189.

What is claimed:

1. An electronic module for an inhaler, the electronic module comprising:
   an electronic module cap comprising a slider guide that protrudes from a top inner surface of the electronic module cap;
   a printed circuit board having a plurality of openings and a switch mounted thereto;
   a slider configured to engage the slider guide, wherein a distal end of the slider engages a yoke of the inhaler such that vertical movement of the yoke is transferred to the slider; and
   a slider spring that is received by the slider guide and engages an upper portion of the slider, the slider spring being configured such that the distal end of the slider is in contact with the yoke,
   wherein the slider is configured to operate the switch when the yoke operates vertically.

2. The electronic module of claim 1, wherein the slider guide comprises:
   a bore that extends from a distal end of the slider guide to the top inner surface of the electronic module cap, and wherein the bore is configured to accept the slider; and
   a channel that extends along a side of the slider guide, wherein the channel is configured to accept an arm of the slider, and wherein the channel comprises a clip that is configured to retain the slider in the slider guide.

3. The electronic module of claim 1, wherein the switch is configured to activate and deactivate the electronic module when operated by the slider.

4. The electronic module of claim 3, wherein the switch provides a wake signal to the electronic module when activated, the wake signal changing the electronics module from a first power state to a second power state.

5. The electronic module of claim 1, wherein the slider comprises a spring seat configured to engage the slider spring, the slider comprising a spring cruciform that extends from the spring seat, and wherein the spring cruciform is configured to extend within and captively engage the slider spring.

6. The electronic module of claim 1, wherein the slider guide comprises a stopper configured to engage a clip of the slider, wherein the stopper limits a vertical travel of the slider when the yoke operates vertically.

7. The electronic module of claim 6, wherein the stopper is configured to limit the vertical travel of the slider after the slider activates the switch.

8. The electronic module of claim 1, wherein the slider is configured to contact the switch when a mouthpiece cover of the inhaler is moved from a closed position to an open position to expose a mouthpiece of the inhaler.

9. An inhaler comprising:
   a mouthpiece;
   a mouthpiece cover;
   an outer housing;
   a yoke;
   a dry powder medicament; and
   an electronic module comprising:
      a slider guide that protrudes from a top inner surface of the inhaler;
      a printed circuit board having a plurality of openings and a switch mounted thereto;
      a slider configured to engage the slider guide, wherein a distal end of the slider engages the yoke such that vertical movement of the yoke is transferred to the slider; and
      a slider spring that is received by the slider guide and engages an upper portion of the slider, the slider spring being configured such that the distal end of the slider is in contact with the yoke,
      wherein the slider is configured to operate the switch when the yoke operates vertically.

10. The inhaler of claim 9, wherein the slider guide comprises a bore that extends from a distal end of the slider guide to the top inner surface inhaler, and wherein the bore is configured to accept the slider.

11. The inhaler of claim 10, wherein the slider guide comprises a channel that extends along a side of the slider guide, and wherein the channel is configured to accept an arm of the slider.

12. The inhaler of claim 11, wherein the channel comprises a clip that is configured to retain the slider in the slider guide.

13. The inhaler of claim 9, wherein the switch is configured to activate and deactivate the electronic module when operated by the slider.

14. The inhaler of claim 13, wherein the switch provides a wake signal to the electronic module when activated, the wake signal changing the electronics module from a first power state to a second power state.

15. The inhaler of claim 9, further comprising a stopper configured to engage a clip of the slider, wherein the stopper is configured to limit the vertical travel of the slider after the slider activates the switch.

16. The inhaler of claim 9, wherein the slider comprises a spring seat configured to engage the slider spring, the slider comprising a spring cruciform that extends from the spring seat, and wherein the spring cruciform is configured to extend within and captively engage the slider spring.

17. The inhaler of claim 9, wherein the electronic module comprises an electronic module cap that is configured to be removably attached to the outer housing of the inhaler; and
   wherein the outer housing comprises an upper housing and a lower housing, the upper housing being configured to engage the electronic module cap, and the lower housing being configured to engage the mouthpiece and the mouthpiece cover.

18. The inhaler of claim 17, wherein the electronic module cap comprises the top inner surface, and wherein the electronic module cap is configured to be removably attached to the outer housing of the inhaler; and
   wherein a top surface of the outer housing comprises an orifice configured to allow the slider to protrude into the outer housing.

19. The inhaler of claim 17, wherein the mouthpiece cover is operably coupled to the slider via the yoke such that the switch is operated by the slider when the mouthpiece cover is opened to an open position such that the mouthpiece is exposed.

20. The electronic module of claim 8, wherein a bellows and a spring are coupled to the mouthpiece cover such that when the mouthpiece cover is moved to expose the mouthpiece the bellows and the spring move in a direction away from the switch.

21. The electronic module of claim 8, wherein the mouthpiece cover is operably coupled to the slider via the yoke such that the switch is operated by the slider when the mouthpiece cover is moved to the open position to expose the mouthpiece.

22. The inhaler of claim 20, wherein the slider is configured to contact the switch when the mouthpiece cover is moved from a closed position to an open position to expose the mouthpiece.

23. A method performed by an inhaler, the method comprising:
  biasing a slider against a yoke using a slider spring such that a distal end of the slider is in contact with the yoke and the vertical movement of the yoke is transferred to the slider;
  translating the yoke vertically as a mouthpiece cover of the inhaler is opened, the slider engaging a slider guide as the yoke translates vertically, wherein the slider guide protrudes from a top inner surface of an electronic module cap of the inhaler;
  the slider activating a switch mounted to a printed circuit board of the inhaler in response to opening of the mouthpiece cover;
  generating a wake message to transition an electronics module of the inhaler to an active state in response to activation of the switch;
  mixing a dry powder medicament with air pulled through the inhaler as a user inhales through the inhaler; and
  when the electronics module is in the active state, monitoring one or more parameters associated with the user's usage and operation of the inhaler.

24. The electronic module of claim 1, wherein the electronic module cap is configured to be removably attached to an outer housing of the inhaler.

25. The electronic module of claim 1, wherein the electronic module cap is permanently attached to an outer housing of the inhaler.

26. The electronic module of claim 25, wherein the outer housing comprises an upper housing and a lower housing, the electronic module cap permanently attached to the upper housing, and the lower housing comprising a mouthpiece and a mouthpiece cover.

* * * * *